United States Patent
Andersen et al.

(10) Patent No.: US 11,072,786 B2
(45) Date of Patent: Jul. 27, 2021

(54) ALPHA-AMYLASE VARIANTS AND POLYNUCLEOTIDES ENCODING SAME

(71) Applicant: Novozymes A/S, Bagsvaerd (DK)

(72) Inventors: Carsten Andersen, Vaerloese (DK); Paria Saunders, Knightdale, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/302,062

(22) PCT Filed: Apr. 10, 2015

(86) PCT No.: PCT/US2015/025342
§ 371 (c)(1),
(2) Date: Oct. 5, 2016

(87) PCT Pub. No.: WO2015/157656
PCT Pub. Date: Oct. 15, 2015

(65) Prior Publication Data
US 2017/0096650 A1    Apr. 6, 2017

Related U.S. Application Data

(60) Provisional application No. 61/977,857, filed on Apr. 10, 2014.

(30) Foreign Application Priority Data

Apr. 20, 2014    (WO) ............... PCT/US2014/033620

(51) Int. Cl.
| | | |
|---|---|---|
| C12N 9/24 | (2006.01) | |
| C12N 1/21 | (2006.01) | |
| C12P 7/06 | (2006.01) | |
| C12P 19/14 | (2006.01) | |
| C11D 3/386 | (2006.01) | |
| C12N 9/28 | (2006.01) | |
| A21D 8/04 | (2006.01) | |
| C12C 5/00 | (2006.01) | |
| D06L 1/14 | (2006.01) | |
| C12P 19/02 | (2006.01) | |

(52) U.S. Cl.
CPC ........... *C12N 9/2417* (2013.01); *A21D 8/042* (2013.01); *C11D 3/386* (2013.01); *C12C 5/004* (2013.01); *C12P 7/06* (2013.01); *C12P 19/02* (2013.01); *C12P 19/14* (2013.01); *C12Y 302/01001* (2013.01); *D06L 1/14* (2013.01); *C12C 2200/05* (2013.01); *C12P 2203/00* (2013.01); *Y02E 50/10* (2013.01)

(58) Field of Classification Search
None
See application file for complete search history.

(56) References Cited

U.S. PATENT DOCUMENTS

| | | | | |
|---|---|---|---|---|
| 7,378,264 | B2* | 5/2008 | Svendsen ............... | C11D 3/386 435/201 |
| 7,498,158 | B2* | 3/2009 | Svendsen ........... | C11D 3/38618 435/202 |
| 9,334,485 | B2* | 5/2016 | Andersen ............... | C12P 19/14 |
| 2002/0155574 | A1* | 10/2002 | Thisted .................. | C11D 3/386 435/202 |
| 2004/0096952 | A1* | 5/2004 | Svendsen ............. | C12N 9/2417 435/202 |
| 2005/0019886 | A1 | 1/2005 | Svendsen et al. | |
| 2010/0099161 | A1* | 4/2010 | Thisted .................. | C11D 3/386 435/196 |
| 2011/0033882 | A1* | 2/2011 | Aehle ..................... | C12P 19/14 435/22 |
| 2014/0017749 | A1 | 1/2014 | Deinhammer et al. | |
| 2014/0206026 | A1* | 7/2014 | Kaasgaard ........... | C12N 9/2414 435/22 |
| 2014/0234906 | A1* | 8/2014 | Andersen ............. | C12N 9/2417 435/69.6 |

FOREIGN PATENT DOCUMENTS

| | | |
|---|---|---|
| WO | 1999/020768 A1 | 4/1999 |
| WO | 2000/29560 A1 | 5/2000 |
| WO | 2002/10355 A2 | 2/2002 |
| WO | 2002/092797 A2 | 11/2002 |
| WO | 2008/153805 A2 | 12/2008 |
| WO | 2010/115021 A2 | 10/2010 |
| WO | 2013/001087 A2 | 1/2013 |
| WO | 2013/057141 A2 | 4/2013 |
| WO | 2013/057143 A2 | 4/2013 |
| WO | 2014/169101 A1 | 10/2014 |

OTHER PUBLICATIONS

Guo et al., Protein tolerance to random amino acid change, Proc. Natl. Acad. Sci. USA, 2004, 101, 9205-10.*
Declerck et al., Hyperthermostabilization of Bacillus licheniformis α-amylase and modulation of its stability over a 50°C temperature range, Protein Eng. 16, 2003, 287-93.*

* cited by examiner

*Primary Examiner* — Robert B Mondesi
*Assistant Examiner* — Todd M Epstein
(74) *Attorney, Agent, or Firm* — David Fazzolare

(57) ABSTRACT

The present invention relates to alpha-amylase variants with improved stability in the presence of glucose and/or relatively higher activity on long chain versus short chain substrates. The present encoding invention also relates to polynucleotides encoding the variants; nucleic acid constructs, vectors, and host cells comprising the polynucleotides; and methods of using the variants.

15 Claims, 4 Drawing Sheets

Specification includes a Sequence Listing.

```
                         1                                                50
SEQ ID NO: 1    (1)   ---ANLNGTLMQYFEWYMPNDGQHWRRLQNDSAYLAEHGITAVWIPPAYK
SEQ ID NO: 2    (1)   --AAPFNGTMMQYFEWYLPDDGTLWTKVANEANNLSSLGITALWLPPAYK
SEQ ID NO: 3    (1)   ANTAPINETMMQYFEWDLPNDGTLWTKVKNEAANLSSLGITALWLPPAYK
SEQ ID NO: 4    (1)   ---VPVNGTMMQYFEWYLPDDGTLWTKVANNAQSLANLGITALWLPPAYK
SEQ ID NO: 5    (1)   -GSVPVNGTMMQYFEWYLPDDGTLWTKVANNAQSLANLGITALWLPPAYK
SEQ ID NO: 6    (1)   -----VNGTLMQYFEWYTPNDGQHWKRLQNDAEHLSDIGITAVWIPPAYK
SEQ ID NO: 7    (1)   -HHNGTNGTMMQYFEWYLPNDGNHWNRLRDDAANLKSKGITAVWIPPAWK
SEQ ID NO: 8    (1)   -HHNGTNGTMMQYFEWHLPNDGNHWNRLRDDASNLRNRGITAIWIPPAWK
SEQ ID NO: 9    (1)   -HHNGTNGTMMQYFEWYLPNDGNHWNRLRSDASNLKDKGISAVWIPPAWK
SEQ ID NO: 10   (1)   -HHNGTNGTMMQYFEWYLPNDGNHWNRLRSDASNLKDKGITAVWIPPAWK
SEQ ID NO: 11   (1)   -HHNGTNGTMMQYYEWYLPNDGNHWNRLNSDASNLKSKGITAVWIPPAWK
SEQ ID NO: 12   (1)   ---DGLNGTMMQYYEWHLENDGQHWNRLHDDAAALSDAGITAIWIPPAYK
SEQ ID NO: 13   (1)   ---ANLNGTLMQYFEWYMPNDGQHWKRLQNDSAYLAEHGITAVWIPPAYK
SEQ ID NO: 14   (1)   -----VNGTLMQYFEWYTPNDGQHWKRLQNDAEHLSDIGITAVWIPPAYK 51                                               100
SEQ ID NO: 1    (48)  GTSQADVGYGAYDLYDLGEFHQKGTVRTKYGTKGELQSAIKSLHSRDINV
SEQ ID NO: 2    (49)  GTSRSDVGYGVYDLYDLGEFNQKGTVRTKYGTKAQYLQAIQAAHAAGMQV
SEQ ID NO: 3    (51)  GTSQSDVGYGVYDLYDLGEFNQKGTIRTKYGTKTQYIQAIQAAKAAGMQV
SEQ ID NO: 4    (48)  GTSSSDVGYGVYDLYDLGEFNQKGTVRTKYGTKTQYIQAIQAAHTAGMQV
SEQ ID NO: 5    (50)  GTSSSDVGYGVYDLYDLGEFNQKGTVRTKYGTKTQYIQAIQAAHTAGMQV
SEQ ID NO: 6    (46)  GLSQSDNGYGPYDLYDLGEFQQKGTVRTKYGTKSELQDAIGSLHSRNVQV
SEQ ID NO: 7    (50)  GTSQNDVGYGAYDLYDLGEFNQKGTVRTKYGTRNQLQAAVTSLKNNGIQV
SEQ ID NO: 8    (50)  GTSQNDVGYGAYDLYDLGEFNQKGTVRTKYGTRSQLESAIHALKNNGVQV
SEQ ID NO: 9    (50)  GASQNDVGYGAYDLYDLGEFNQKGTIRTKYGTRNQLQAAVNALKSNGIQV
SEQ ID NO: 10   (50)  GASQNDVGYGAYDLYDLGEFNQKGTVRTKYGTRNQLQAAVTALKSNGIQV
SEQ ID NO: 11   (50)  GASQNDVGYGAYDLYDLGEFNQKGTVRTKYGTRSQLQAAVTSLKNNGIQV
SEQ ID NO: 12   (48)  GNSQADVGYGAYDLYDLGEFNQKGTVRTKYGTKAQLERAIGSLKSNDINV
SEQ ID NO: 13   (48)  GTSQADVGYGAYDLYDLGEFHQKGTVRTKYGTKGELQSAIKSLHSRDINV
SEQ ID NO: 14   (46)  AISQADVGYGAYDLYDLGEFHQKGTVRTKYGTKGELQSAIKSLHSRDINV 101                                              150
SEQ ID NO: 1    (98)  YGDVVINHKGGADATEDVTAVEVDPADRNRVISGEHLIKAWTHFHFPGRG
SEQ ID NO: 2    (99)  YADVVFDHKGGADGTEWVDAVEVNPSDRNQEISGTYQIQAWTKFDFPGRG
SEQ ID NO: 3    (101) YADVVFNHKAGADGTEFVDAVEVDPSNRNQETSGTYQIQAWTKFDFPGRG
SEQ ID NO: 4    (98)  YADVVFNHKAGADGTELVDAVEVNPSDRNQEISGTYQIQAWTKFDFPGRG
SEQ ID NO: 5    (100) YADVVFNHKAGADGTELVDAVEVNPSDRNQEISGTYQIQAWTKFDFPGRG
SEQ ID NO: 6    (96)  YGDVVLNHKAGADATEDVTAVEVNPANRNQETSEEYQIKAWTDFRFPGRG
SEQ ID NO: 7    (100) YGDVVMNHKGGADGTEIVNAVEVNRSNRNQETSGEYAIEAWTKFDFPGRG
SEQ ID NO: 8    (100) YGDVVMNHKGGADATENVLAVEVNPNNRNQEISGDYTIEAWTKFDFPGRG
SEQ ID NO: 9    (100) YGDVVMNHKGGADATEMVRAVEVNPNNRNQEVSGEYTIEAWTKFDFPGRG
SEQ ID NO: 10   (100) YGDVVMNHKGGADATEWVRAVEVNPSNRNQEVSGDYTIEAWTKFDFPGRG
SEQ ID NO: 11   (100) YGDVVMNHKGGADATEMVRAVEVNPNNRNQEVTGEYTIEAWTRFDFPGRG
SEQ ID NO: 12   (98)  YGDVVMNHKMGADFTEAVQAVQVNPTNRWQDISGAYTIDAWTGFDFSGRN
SEQ ID NO: 13   (98)  YGDVVINHKGGADATEDVTAVEVDPADRNRVISGEYLIKAWTHFHFPGRG
SEQ ID NO: 14   (96)  YGDVVINHKAGADATEDVTAVEVDPADRNRVISGEHLIKAWTHFHFPGRG
```

Fig. 1

```
                   151                                              200
SEQ ID NO: 1  (148) STYSDFKWHWYHFDGTDWDESR-KLNRIYKFQG--KAWDWEVSNENGNYD
SEQ ID NO: 2  (149) NTYSSFKWRWYHFDGVDWDESR-KLSRIYKFRGIGKAWDWEVDTENGNYD
SEQ ID NO: 3  (151) NTYSSFKWRWYHFDGTDWDESR-KLNRIYKFRSTGKAWDWEVDTENGNYD
SEQ ID NO: 4  (148) NTYSSFKWRWYHFDGTDWDESR-KLNRIYKFRGTGKAWDWEVDTENGNYD
SEQ ID NO: 5  (150) NTYSSFKWRWYHFDGTDWDESR-KLNRIYKFRGTGKAWDWEVDTENGNYD
SEQ ID NO: 6  (146) NTYSDFKWHWYHFDGADWDESR-KISRIFKFRGEGKAWDWEVSSENGNYD
SEQ ID NO: 7  (150) NNHSSFKWRWYHFDGTDWDQSRQLQNKIYKFRGTGKAWDWEVDTENGNYD
SEQ ID NO: 8  (150) NTYSDFKWRWYHFDGVDWDQSRQFQNRIYKFRGDGKAWDWEVDSENGNYD
SEQ ID NO: 9  (150) NTHSNFKWRWYHFDGVDWDQSRKLNNRIYKFRGDGKGWDWEVDTENGNYD
SEQ ID NO: 10 (150) NTHSNFKWRWYHFDGVDWDQSRQLQNRIYKFRGDGKGWDWEVDTENGNYD
SEQ ID NO: 11 (150) NTHSSFKWRWYHFDGVDWDQSRRLNNRIYKFRGHGKAWDWEVDTENGNYD
SEQ ID NO: 12 (148) NAYSDFKWRWFHFNGVDWDQRY-QENHIFRFAN--TNWNWRVDEENGNYD
SEQ ID NO: 13 (148) STYSDFKWYWYHFDGTDWDESR-KLNRIYKFQG--KYWDWEVSNENGNYD
SEQ ID NO: 14 (146) STYSDFKWYWYHFDGTDWDESR-KLNRIYKFQG--KTWDWEVSNEFGNYD 201                                              250
SEQ ID NO: 1  (195) YLMYADIDYDHPDVAAEIKRWGTWYANELQLDGFRLDAVKHIKFSFLRDW
SEQ ID NO: 2  (198) YLMYADLDMDHPEVVTELKNWGKWYVNTTNIDGFRLDAVKHIKFSFFPDW
SEQ ID NO: 3  (200) YLMFADLDMDHPEVVTELKNWGTWYVNTTNIDGFRLDAVKHIKYSFFPDW
SEQ ID NO: 4  (197) YLMYADLDMDHPEVSELKNWGKWYVTTTNIDGFRLDAVKHIKYSFFPDW
SEQ ID NO: 5  (199) YLMYADLDMDHPEVSELKNWGKWYVITTNIDGFRLDAVKHIKYSFFPDW
SEQ ID NO: 6  (195) YLMYADVDYDHPDVVAETKKWGIWYANELSLDGFRIDAAKHIKFSFLRDW
SEQ ID NO: 7  (200) YLMYADVDMDHPEVIHELRNWGVWYTNTLNLDGFRIDAVKHIKYSFTRDW
SEQ ID NO: 8  (200) YLMYADVDMDHPEVNELRRWGEWYTNTLNLDGFRIDAVKHIKYSFTRDW
SEQ ID NO: 9  (200) YLMYADIDMDHPEVVNELRNWGVWYTNTLGLDGFRIDAVKHIKYSFTRDW
SEQ ID NO: 10 (200) YLMYADIDMDHPEVVNELRNWGVWYTNTLGLDGFRIDAVKHIKYSFTRDW
SEQ ID NO: 11 (200) YLMYADIDMDHPEVVNELRNWGVWYTNTLGLDGFRIDAVKHIKYSFTRDW
SEQ ID NO: 12 (195) YLLGSNIDFSHPEVQDELKDWGSWFTDELDLDGYRLDAIKHIPFWYTSDW
SEQ ID NO: 13 (195) YLMYADIDYDHPDVVAEIKRWGTWYANELQLDGNRLDAVKHIKFSFLRDW
SEQ ID NO: 14 (193) YLMYADFDYDHPDVVAEIKRWGTWYANELQLDGFRLDAVKHIKFSFLRDW 251                                              300
SEQ ID NO: 1  (245) VNHVREKTGKEMFTVAEYWQNDLGALENYLNKTNFNHSVFDVPLHYQFHA
SEQ ID NO: 2  (248) LSYVRSQTGKPLFTVGEYWSYDINKLHNYITKTNGTMSLFDAPLHNKFYT
SEQ ID NO: 3  (250) LTYVRNQTGKNLFAVGEFWSYDVNKLHNYITKTNGSMSLFDAPLHNNFYT
SEQ ID NO: 4  (247) LSYVRTQTQKPLFAVGEFWSYDISKLHNYITKTNGSMSLFDAPLHNNFYI
SEQ ID NO: 5  (249) LSYLRTQTQKPLFAVGEFWSYDINKLHNYITKTNGSMSLFDAPLHNNFYI
SEQ ID NO: 6  (245) VQAVRQATGKEMFTVAEYWQNNAGKLENYLNKTSFNQSVFDVPLHFNLQA
SEQ ID NO: 7  (250) LTHVRNTTGKPMFAVAEFWKNDLGAIENYLNKTSWNHSVFDVPLHYNLYN
SEQ ID NO: 8  (250) LTHVRNATGKEMFAVAEFWKNDLGALENYLNKTNWNHSVFDVPLHYNLYN
SEQ ID NO: 9  (250) INHVRSATGKNMFAVAEFWKNDLGAIENYLNKTNWNHSVFDVPLHYNLYN
SEQ ID NO: 10 (250) LTHVRNTTGKNMFAVAEFWKNDIGAIENYLSKTNWNHSVFDVPLHYNLYN
SEQ ID NO: 11 (250) INHVRSATGKNMFAVAEFWKNDLGAIENYLQKTNWNHSVFDVPLHYNLYN
SEQ ID NO: 12 (245) VRHQRNEADQDLFVVGEYWKDDVGALEFYLDEMNWEMSLFDVPLNYNFYR
SEQ ID NO: 13 (245) VNHVREKTGKEMFTVAEYWQNDLGALENYLNKTNFNHSVFDVPLHYQFYA
SEQ ID NO: 14 (243) VNHVREKTGKEMFTVAEYWSNDLGALENYLNKTNFNHSVFDVPLHYQFHA
```

Fig. 1 cont.

```
                    301                                                 350
SEQ ID NO: 1  (295) ASTQGGGYDMRKLLNGTVVSKHPLKSVTFVDNHDTQPGQSLESTVQTWFK
SEQ ID NO: 2  (298) ASKSGGAFDMRTLMTNTLMKDQPTLAVTFVDNHDTEPGQALQSWVDPWFK
SEQ ID NO: 3  (300) ASKSSGYFDMRYLLNNTLMKDQPSLAVTLVDNHDTQPGQSLQSWVEPWFK
SEQ ID NO: 4  (297) ASKSGGYFDMRTLLNNTLMKDQPTLAVTLVDNHDTEPGQSLQSWVEPWFK
SEQ ID NO: 5  (299) ASKSGGYFDMRTLLNNTLMKEQPTLSVTLVDNHDTEPGQSLQSWVEPWFK
SEQ ID NO: 6  (295) ASSQGGGYDMRRLLDGTVVSRHPEKAVTFVENHDTQPGQSLESTVQTWFK
SEQ ID NO: 7  (300) ASNSGGYYDMRNILNGSVVQKHPTHAVTFVDNHDSQPGEALESFVQQWFK
SEQ ID NO: 8  (300) ASNSGGNYDMAKLLNGTVVQKHPMHAVTFVDNHDSQPGESLESFVQEWFK
SEQ ID NO: 9  (300) ASKSGGNYDMRQIFNGTVVQRHPMHAVTFVDNHDSQPEEALESFVEEWFK
SEQ ID NO: 10 (300) ASRSGGNYDMRQIFNGTVVQRHPTHAVTFVDNHDSQPEEALESFVEEWFK
SEQ ID NO: 11 (300) ASKSGGNYDMRNIFNGTVVQRHPSHAVTFVDNHDSQPEEALESFVEEWFK
SEQ ID NO: 12 (295) ASQQGGSYDMRNILRGSLVEAHPMHAVTFVDNHDTQPGESLESWVADWFK
SEQ ID NO: 13 (295) ASTQGGGYDMRKLLNDTVVSKHPLKSVTFVDNHDTQPGQSLESTVQTWFK
SEQ ID NO: 14 (293) ASTQGGGYDMRKLLNGTVVSKHPLKSVTFVDNHDTQPGQSLESTVQTWFK 351                                                 400
SEQ ID NO: 1  (345) PLAYAFILTRESGYPQVFYGDMYGTKGDSQREIPALKHKIEPILKARKQY
SEQ ID NO: 2  (348) PLAYAFILTRQEGYPCVFYGDYYGIPQYN---IPSLKSIDPLLIARRDY
SEQ ID NO: 3  (350) PLAYAFILTRQEGYPCVFYGDYYGIPKYN---IPGLKSIDPLLIARRDY
SEQ ID NO: 4  (347) PLAYAFILTRQEGYPCVFYGDYYGIPKYN---IPALKSLDPLLIARRDY
SEQ ID NO: 5  (349) PLAYAFILTRQEGYPCVFYGDYYGIPKYN---IPALKSLDPLLIARRDY
SEQ ID NO: 6  (345) PLAYAFILTRESGYPQVFYGDMYGTKGTSPKEIPSLKDNIEPILKARKEY
SEQ ID NO: 7  (350) PLAYALVLTREQGYPSVFYGDYYGIPTHG---VPAMKSIDPLLQARQTF
SEQ ID NO: 8  (350) PLAYALILTREQGYPSVFYGDYYGIPTHS---VPAMKAKIDPILEARQNF
SEQ ID NO: 9  (350) PLAYALTLTREQGYPSVFYGDYYGIPTHG---VPAMKSKIDPILEARQKY
SEQ ID NO: 10 (350) PLACALTLTRDQGYPSVFYGDYYGIPTHG---VPAMKSKIDPILEARQKY
SEQ ID NO: 11 (350) PLAYALTLTREQGYPSVFYGDYYGIPTHG---VPAMRSKIDPILEARQKY
SEQ ID NO: 12 (345) PLAYATILTREGGYPNVFYGDYYGIPNDN---ISAKKDMIDELLDARQNY
SEQ ID NO: 13 (345) PLAYAFILTRESGYPQVFYGDMYGTKGDSQREIPALKHKIEPILKARKQY
SEQ ID NO: 14 (343) PLAYAFILTRESGYPQVFYGDMYGTKGDSQREIPALKHKIEPILKARKQY 401                                                 450
SEQ ID NO: 1  (395) AYGAQHDYFDHHDIVGWTREGDSSVANSGLAALITDGPGGAKRMYVGRQN
SEQ ID NO: 2  (395) AYGTQHDYLDHSDIIGWTREGVTEKPGSGLAALITDGPGGSKWMYVGKQH
SEQ ID NO: 3  (397) AYGTQRDYIDHQDIIGWTREGIDTKPNSGLAALITDGPGGSKWMYVGKKH
SEQ ID NO: 4  (394) AYGTQHDYIDSADIIGWTREGVAEKANSGLAALITDGPGGSKWMYVGKQH
SEQ ID NO: 5  (396) AYGTQHDYIDNADIIGWTREGVAEKANSGLAALITDGPGGSKWMYVGKQH
SEQ ID NO: 6  (395) AYGPQHDYIDPDVIGWTREGDSSAAKSGLAALITDGPGGSKRMYAGLKN
SEQ ID NO: 7  (397) AYGTQHDYFDHHDIIGWTREGNSSHPNSGLATIMSDGPGGNKWMYVGKNK
SEQ ID NO: 8  (397) AYGTQHDYFDHHNIIGWTREGNTHPNSGLATIMSDGPGGEKWMYVGQNK
SEQ ID NO: 9  (397) AYGRQNDYLDHHNIIGWTREGNTAHPNSGLATIMSDGAGGNKWMFVGRNK
SEQ ID NO: 10 (397) AYGKQNDYLDHHNMIGWTREGNTAHPNSGLATIMSDGPGGNKWMYVGRNK
SEQ ID NO: 11 (397) AYGKQNDYLDHHNIIGWTREGNTAHPNSGLATIMSDGAGGSKWMFVGRNK
SEQ ID NO: 12 (392) AYGTQHDYFDHWDVVGWTREGSSSRPNSGLATIMSNGPGGSKWMYVGRQN
SEQ ID NO: 13 (395) AYGAQHDYFDHHDIVGWTREGDSSVANSGLAALITDGPGGAKRMYVGRQN
SEQ ID NO: 14 (393) AYGAQHDYFDHHDIVGWTREGDSSVANSGLAALITDGPGGAKRMYVGRQN
```

Fig. 1 cont.

```
                     451                                             500
SEQ ID NO: 1   (445) AGETWHDITGNRSEPVVINSEGWGEFHVNGGSVSIYVQR-----------
SEQ ID NO: 2   (445) AGKVFYDLTGNRSDTVTINSDGWGEFKVNGGSVSVWVPRKTT---VSTIA
SEQ ID NO: 3   (447) AGKVFYDLTGNRSDTVTINADGWGEFKVNGGSVSIWVAKTSN---VTFTV
SEQ ID NO: 4   (444) AGKTFYDLTGNRSDTVTINADGWGEFKVNGGSVSIWVPKISTTSQITFTV
SEQ ID NO: 5   (446) AGKTFYDLTGNRSDTVTINADGWGEFKVNGGSVSIWVPKTSTTSQITFTV
SEQ ID NO: 6   (445) AGETWYDITGNRSDTVKIGSDGWGEFHVNDGSVSIYVQK-----------
SEQ ID NO: 7   (447) AGQVWRDITGNRTGTVTINADGWGNFSVNGGSVSVWVKQ-----------
SEQ ID NO: 8   (447) AGQVWHDITGNKPGTVTINADGWANFSVNGGSVSIWVKR-----------
SEQ ID NO: 9   (447) AGQVWTDITGNRAGTVTINADGWGNFSVNGGSVSIWVNK-----------
SEQ ID NO: 10  (447) AGQVWRDITGNRSGTVTINADGWGNFSVNGGSVSIWVNN-----------
SEQ ID NO: 11  (447) AGQVWSDITGNRTGTVTINADGWANFSVNGGSVSIWVNK-----------
SEQ ID NO: 12  (442) AGQTWTDLTGNNGASVTINGDGWGEFFTNGGSVSVYVNQ-----------
SEQ ID NO: 13  (445) AGETWYDITGNRSEPVVINSEGWGEFHVNDGSVSIYVQR-----------
SEQ ID NO: 14  (443) AGETWHDITGNRSEPVVINSEGWGEFHVNGGSVSIYVQR-----------

501                                             550
SEQ ID NO: 1   (484) --------------------------------------------------
SEQ ID NO: 2   (492) RPITTRPWTGEFVRWTEPRLVAWP--------------------------
SEQ ID NO: 3   (494) NNATTTSGQNVYVVANIPELGNWNTANAIKMNPSSYPTWKATIALPQGKA
SEQ ID NO: 4   (494) NNATTVWGQNVYVVGNISQLGNWDPVHAVQMTPSSYPTWTVTIPLLQGQN
SEQ ID NO: 5   (496) NNATTVWGQNVYVVGNISQLGNWDPVNAVQMTPSSYPTWVVTVPLPQSQN
SEQ ID NO: 6   (484) --------------------------------------------------
SEQ ID NO: 7   (486) --------------------------------------------------
SEQ ID NO: 8   (486) --------------------------------------------------
SEQ ID NO: 9   (486) --------------------------------------------------
SEQ ID NO: 10  (486) --------------------------------------------------
SEQ ID NO: 11  (486) --------------------------------------------------
SEQ ID NO: 12  (481) --------------------------------------------------
SEQ ID NO: 13  (484) --------------------------------------------------
SEQ ID NO: 14  (482) --------------------------------------------------

551                                      591
SEQ ID NO: 1   (484) -----------------------------------------
SEQ ID NO: 2   (516) -----------------------------------------
SEQ ID NO: 3   (544) IEFKFIKKDQAGNVIWESTSNRTYTVPFSSTGSYTASWNVP
SEQ ID NO: 4   (544) IQFKFIKKDSAGNVIWEDISNRTYTVPTAASGAYTASWNVP
SEQ ID NO: 5   (546) IQFKFIKKDGSGNVIWENISNRTYTVPTAASGAYTANWNVP
SEQ ID NO: 6   (484) -----------------------------------------
SEQ ID NO: 7   (486) -----------------------------------------
SEQ ID NO: 8   (486) -----------------------------------------
SEQ ID NO: 9   (486) -----------------------------------------
SEQ ID NO: 10  (486) -----------------------------------------
SEQ ID NO: 11  (486) -----------------------------------------
SEQ ID NO: 12  (481) -----------------------------------------
SEQ ID NO: 13  (484) -----------------------------------------
SEQ ID NO: 14  (482) -----------------------------------------
```

ALPHA-AMYLASE VARIANTS AND POLYNUCLEOTIDES ENCODING SAME

CROSS-REFERENCE TO RELATED APPLICATIONS

This application is a 35 U.S.C. 371 national application of PCT/US2015/025342 filed Apr. 10, 2015, which claims priority or the benefit under 35 U.S.C. 119 of US PCT application No. PCT/US2014/033620 filed Apr. 10, 2014 and U.S. provisional application No. 61/977,857 filed Apr. 10, 2014, the contents of which are fully incorporated herein by reference.

REFERENCE TO A SEQUENCE LISTING

This application contains a sequence listing that was submitted as an ASCII text file named SQText.txt (created on Apr. 10, 2015, containing 65 kb), which is incorporated by reference herein in its entirety.

BACKGROUND OF THE INVENTION

Field of the Invention

The present invention relates to alpha-amylase variants, polynucleotides encoding the variants, methods of producing the variants, and methods of using the variants.

Description of the Related Art

Alpha-amylases (E.C. 3.2.1.1) constitute a group of enzymes which catalyze hydrolysis of starch, glycogen and related polysaccharides and oligosaccharides.

Alpha-amylases are used commercially for a variety of purposes such as in the initial stages of starch processing, such as liquefaction; in wet milling processes; and in ethanol production from carbohydrate sources. Alpha-amylases are also used as cleaning agents or adjuncts in detergent matrices; in the textile industry for starch desizing; in baking applications; in the beverage industry; in oil fields in drilling processes; in recycling processes, e.g., for de-inking paper; and in animal feed.

Some commercial alpha-amylases for, e.g., starch liquefaction originate from bacteria, such as *Bacillus licheniformis* and *Bacillus stearothermophilus*. Protein engineered variants have been developed to overcome stability issues at low pH and high temperature, in particular at low calcium concentrations. Today, some such liquefactions are run at a low Sodium ion concentrations. Thus, there is a need for alpha-amylases with improved stability in processes (e.g., liquefaction) carried out at low sodium ion concentrations, low pH and high temperature, in particular at low calcium concentrations.

WO 2013/057141 and WO 2013/057143 describe bacterial alpha-amylase variants with improved stability at low pH and high temperature, in particular at low calcium concentrations.

It is an object of the present invention to provide alpha-amylase variants.

SUMMARY OF THE INVENTION

The present invention relates to alpha-amylase variants with improved stability in the presence of glucose and/or relatively higher activity on long chain versus short chain substrates.

In one aspect the invention relates to alpha-amylase variants of parent alpha-amylases comprising one or more substitutions, using SEQ ID NO: 1 for numbering, or corresponding substitutions, in groups a) and b):

group a) K176, E185, I201, H205, K213, Q360, D416, R437;

group b) substitution of an additional lysine residue to a non-native amino acid; wherein the variant has at least 80%, but less than 100% sequence identity to:

(i) the mature polypeptide of any of SEQ ID NOs: 1 or 14, or (ii) amino acids 1 to 483 of SEQ ID NO: 1 or amino acids 1 to 481 of SEQ ID NO: 14; and wherein the variant has alpha-amylase activity.

The alpha-amylase may be of any origin, such as bacterial origin, especially *Bacillus* origin, such as *Bacillus licheniformis* origin.

In a preferred embodiment the alpha-amylase variant comprises or has the following or corresponding group a) and group b) substitutions:

group a): K176L+E185P+I201Y+H205Y+K213T+Q360S+D416V+R437W; and one or more of the following substitutions in group b):
K136, K154, K170, K234, K237, K251, K315, K319, K392 (using SEQ ID NO: 1 for numbering).

In a preferred embodiment the alpha-amylase variant comprises or has the following or corresponding group a) and group b) substitutions:

group a): K176L+E185P+I201Y+H205Y+K213T+Q360S+D416V+R437W; and
one or more of the following substitutions in group b):
K136R, K154A, K154H, K154S, K170R, K170S, K234T, K237R, K251Q, K315M, K319Q, K319L, K392V (using SEQ ID NO: 1 for numbering).

As can be seens from the alignment in FIG. 1 group a) positions in SEQ ID NO: 1, i.e., K176, E185, I201, H205, K213, Q360, D416, R437, correspond to K174, E183, F199, H203, K211, Q358, D414, R435W in SEQ ID NO: 14.

In an embodiment the alpha-amylase variant comprises or has the following or corresponding group a) and group b) substitutions:

group a): K174L+E183P+F199Y+H203Y+K211T+Q358S+D414V+R435W; and one or more of the following substitutions in group b):
K134, K152, K168, K232, K235, K249, K313, K317, K390 (using SEQ ID NO: 14 for numbering).

In an embodiment the alpha-amylase variant comprises or has the following or corresponding group a) and group b) substitutions:

group a): K174L+E183P+F199Y+H203Y+K211T+Q358S+D414V+R435W; and
one or more of the following substitutions in group b):
K134R, K152A, K152H, K152S, K168R, K168S, K232T, K235R, K249Q, K313M, K317Q, K317L, K390V (using SEQ ID NO: 14 for numbering).

A variant of the invention has improved stability, in particular improved stability in the presence of glucose compared to the mature polypeptide of SEQ ID NO: 1 or 14, respectively. A variant of the invention has a relatively higher activity on long chain versus short chain substrates as compared to the mature polypeptide of SEQ ID NO: 1 or 14, respectively.

In one aspect the invention relates to isolated polynucleotide encoding the variant of the invention.

In one aspect the invention relates to nucleic acid constructs comprising the polynucleotide of the invention.

In one aspect the invention relates to expression vectors comprising a polynucleotide of or construct of the invention.

In one aspect the invention relates to a host cell comprising the polynucleotide of the invention.

In one aspect the invention relates to methods of producing alpha-amylase variants, comprising:
a. cultivating the host cell of the invention under conditions suitable for expression of the variant; and
b. recovering the variant.

In one aspect the invention relates to methods for obtaining alpha-amylase variants of the invention, comprising (a) introducing into a parent alpha-amylase a substitution as defined above; and (b) recovering the variant.

In one aspect the invention relates to compositions comprising a variant of the invention and one or more enzymes selected from the group consisting of beta-amylase, cellulase (beta-glucosidase, cellobiohydrolase, and endoglucanase) glucoamylase, hemicellulase (e.g., xylanase), isoamylase, isomerase, lipase, phytase, protease and pullulanase. In an embodiment an additional alpha-amylase, i.e., a second alpha-amylase, may be added. In an embodiment the additional alpha-amylase may be an alpha-amylase of another origin. When the alpha-amylase variant of the invention is of the parent alpha-amylase shown in SEQ ID NO: 1 (i.e., *Bacillus licheniformis* alpha-amylase) the additional alpha-amylase may be a *Bacillus stearothermophilus* alpha-amylase. When the alpha-amylase variant of the invention is the parent alpha-amylase shown in SEQ ID NO: 14 (i.e., hybrid alpha-amylase of *Bacillus amyloliquefaciens* alpha-amylase shown in SEQ ID NO: 6 and a variant of the *Bacillus licheniformis* alpha-amylase shown in SEQ ID NO: 1 or LE399) the additional/second alpha-amylase may be a *Bacillus stearothermophilus* alpha-amylase, such as the mature part of the alpha-amylase disclosed in WO 2002/010355 as SEQ ID NO: 6, or a variant thereof.

In one aspect the invention relates to methods of producing liquefied starch, comprising liquefying a starch-containing material with the variant of the invention or a composition of the invention.

In one aspect the invention relates to processes of producing a fermentation product, especially ethanol, comprising
(a) liquefying a starch-containing material with the variant of the invention to produce a liquefied mash;
(b) saccharifying the liquefied mash to produce fermentable sugars; and
(c) fermenting the fermentable sugars using a fermenting organism.

In one aspect the invention relates to processes of producing a sugars, comprising
(a) liquefying a starch-containing material with the variant of the invention to produce a liquefied mash;
(b) saccharifying the liquefied mash to produce fermentable sugars.

In an embodiment the produced sugars may be recovered. The sugars may also be converted to other end products, such as syrups. In an embodiment the sugars are isomerized into fructose or fructose containing product, such as High Fructose Syrup, especially High Fructose Corn Syrup (HFCS) and/or maltose syrup.

In one aspect the invention relates to the use of the variants of the invention for washing and/or dishwashing.

In one aspect the invention relates to the use of the variants of the invention for desizing a textile.

In one aspect the invention relates to the use of the variants of the invention for producing a baked product.

In one aspect the invention relates to the use of the variants of the invention for liquefying a starch-containing material.

In one aspect the invention relates to the use of the variants of the invention for liquefying a starch-containing material in a process of producing syrups.

In one aspect the invention relates to the use of the variants of the invention for liquefying a starch-containing material in a process of producing a fermentation product, such as ethanol.

BRIEF DESCRIPTION OF THE FIGURES

FIG. 1 shows an alignment of alpha-amylases with the amino acid sequences of:
SEQ ID NO: 1 is a *Bacillus licheniformis* alpha-amylase.
SEQ ID NO: 2 is a *Bacillus stearothermophilus* alpha-amylase.
SEQ ID NO: 3 is the *Bacillus* alpha-amylase TS-23 described in J. Appl. Microbiology, 1997, 82: 325-334 (SWALL:q59222).
SEQ ID NO: 4 is *Bacillus flavothermus* alpha-amylase AMY1048 described in WO 2005/001064.
SEQ ID NO: 5 is *Bacillus* alpha-amylase TS-22 described as SEQ ID NO: 21 in WO 04/113511.
SEQ ID NO: 6 is a *Bacillus amyloliquefaciens* alpha-amylase.
SEQ ID NO: 7 is *Bacillus* alkaline sp. SP690 amylase described as SEQ ID NO 1 in WO 95/26397.
SEQ ID NO: 8 is *Bacillus halmapalus* alpha-amylase described as SEQ ID NO 2 in WO 95/26397.
SEQ ID NO: 9 is *Bacillus* alkaline sp. AA560 amylase described as SEQ ID NO 4 in WO 00/60060.
SEQ ID NO: 10 is *Bacillus* alkaline sp. A 7-7 amylase described as SEQ ID NO 2 in WO200210356.
SEQ ID NO: 11 is *Bacillus* alkaline sp. SP707 amylase described in Tsukamoto et al., 1988, *Biochem. Biophys. Res. Commun.* 151: 25-33).
SEQ ID NO: 12 is *Bacillus* alkaline sp. K-38 amylase described as SEQ ID NO 2 in EP 1022334.
SEQ ID NO: 13 is a *Bacillus licheniformis* alpha-amylase described in Lee et al, 2006, J. Biochem, 139: 997-1005.
SEQ ID NO: 14 is a variant alpha-amylase LE399 previously disclosed in, e.g., WO 2002/010355.
SEQ ID NO: 15 is a variant alpha-amylase: LE2488.

DEFINITIONS

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-amylase: Alpha-amylases (E.C. 3.2.1.1) are a group of enzymes which catalyze the hydrolysis of starch and other linear and branched 1,4 glucosidic oligo- and polysaccharides. The skilled person will know how to determine alpha-amylase activity. It may be determined according to the procedure described in the Examples, e.g., by the PNP-G7 assay. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1 or SEQ ID NO: 14. In another aspect, a variant of the present application has at least 20%, e.g., at least 40%, at least 50%, at least 60%, at least 70%, at least 80%, at least 90%, at least 95%, or at least 100% of the alpha-amylase activity of its parent.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has alpha-amylase activity. In one aspect, a fragment contains at least 300 amino acid residues, at least 350 amino acid residues, at least 400 amino acid residues, at least 450 amino acid residues, at least 470 amino acid residues, or at least 480 amino acid residues.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two or more different mature polypeptides (i.e., with a different C-terminal and/or N-terminal amino acid) expressed by the same polynucleotide. The mature form of some alpha-amylases, e.g., some bacterial alpha-amylases, comprises a catalytic domain containing the active site for substrate hydrolysis and one or more carbohydrate-binding modules (CBM) for binding to the carbohydrate substrate (starch) and optionally a polypeptide linking the CBM(s) with the catalytic domain, a region of the latter type usually being denoted a "linker".

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent alpha-amylase: The term "parent" or "parent alpha-amylase" means an alpha-amylase to which an alteration is made to produce the alpha-amylase variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g., several) amino acids, e.g., 1-5 amino acids, adjacent to the amino acid occupying a position. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1. In another aspect, a variant of the present application has at least 20%, e.g., at least 40%, at least 50%, at least 60%, at least 70%, at least 80%, at least 90%, at least 95%, or at least 100% of the alpha-amylase activity of its parent. The alpha-amylase activity may be determined by the PNP-G7 assay described in the Examples.

Wild-type alpha-amylase: The term "wild-type" alpha-amylase means an alpha-amylase expressed by a naturally occurring microorganism, such as a bacterium, yeast, or filamentous fungus found in nature.

The term "granular starch" is understood as raw uncooked starch, i.e. starch that has not been subjected to a gelatinization. Starch is formed in plants as tiny granules insoluble in water. These granules are preserved in starches at temperatures below the initial gelatinization temperature. When put in cold water, the grains may absorb a small amount of the liquid. Up to 50° C. to 70° C. the swelling is reversible, the degree of reversibility being dependent upon the particular starch. With higher temperatures an irreversible swelling called gelatinization begins.

The term "initial gelatinization temperature" is understood as the lowest temperature at which gelatinization of the starch commences. Starch begins to gelatinize between 60° C. and 70° C., the exact temperature dependent on the specific starch. The initial gelatinization temperature depends on the source of the starch to be processed. The initial gelatinization temperature for wheat starch is approximately 52° C., for potato starch approximately 56° C., and for corn starch approximately 62° C. However, the quality of the starch initial may vary according to the particular variety of the plant species as well as with the growth conditions and therefore initial gelatinization temperature should be determined for each individual starch lot.

The term "soluble starch hydrolysate" is understood as the soluble products of the processes of the invention and may comprise mono- di-, and oligosaccharides, such as glucose, maltose, maltodextrins, cyclodextrins and any mixture of these. Preferably at least 90%, 91%, 92%, 93%, 94%, 95%, 96%, 97% or 98% of the dry solids of the granular starch is converted into a soluble starch hydrolysate.

The term "Speciality Syrups", is an in the art recognised term and is characterised according to DE and carbohydrate spectrum (See the article "New Speciality Glucose Syrups", p. 50+, in the textbook "Molecular Structure and Function of Food Carbohydrate", Edited by G. G. Birch and L. F. Green, Applied Science Publishers LTD., London). Typically Speciality Syrups have a DE in the range from 35 to 45.

Glucoamylase activity: The term "glucoamylase activity" means 1,4-alpha-D-glucan glucohydrolase activity, (EC 3.2.1.3) that catalyzes the release of D-glucose from the non-reducing ends of starch or related oligo- and polysaccharide molecules. For purposes of the present invention, glucoamylase activity is determined according to the procedure described in the "Materials and Methods"-section below. The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

Beta-amylase activity: The term "beta-amylase activity" means 4-alpha-D-glucan maltohydrolase activity (EC 3.2.1.2), which catalyzes the hydrolysis of (1->4)-alpha-D-glucosidic linkages in polysaccharides so as to remove successive maltose units from the non-reducing ends of the chains until the molecule is degraded or, in the case of amylopectin, until a branch point is reached. The maltose released has the beta anomeric configuration, hence the name beta-amylase. Beta-amylase is the name traditionally given to exo-acting maltogenic amylases, which catalyze the hydrolysis of 1,4-alpha-glucosidic linkages in amylose, amylopectin and related glucose polymers. For purposes of the present invention, beta-amylase activity is determined according to the procedure described in the "Materials and Methods" section below.

CONVENTIONS FOR DESIGNATION OF VARIANTS

For purposes of the present invention, the mature polypeptide disclosed in SEQ ID NO: 1 is used to determine the corresponding amino acid residue in other alpha-amylases. The amino acid sequence of another alpha-amylase is aligned with the mature polypeptide disclosed in SEQ ID NO: 1, and based on the alignment, the amino acid position number corresponding to any amino acid residue in the mature polypeptide disclosed in SEQ ID NO: 1, is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

For instance, FIG. 1 shows that K176, E185, I201, H205, K213, Q360, D416, R437 in SEQ ID NO: 1 corresponds to K174, E183, F199, H203Y, K211, Q358, D414, R435 in SEQ ID NO: 14.

When the other enzyme has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. In the Examples of the present application, multiple mutations are separated by a space, e.g., G205R S411F representing G205R+S411F.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to alpha-amylase variants with improved stability in the presence of glucose and/or relatively higher activity on long chain versus short chain substrates.

Variants

In one aspect the invention relates to alpha-amylase variants of parent alpha-amylases comprising one or more substitutions, using SEQ ID NO: 1 for numbering, or corresponding substitutions, in groups a) and b):

group a) K176, E185, I201, H205, K213, Q360, D416, R437;

group b) a substitution of lysine to a non-native amino acid;

wherein the variant has at least 80%, but less than 100% sequence identity to:

(i) the mature polypeptide of any of SEQ ID NOs: 1 or 14, or (ii) amino acids 1 to 483 of SEQ ID NO: 1 or amino acids 1 to 481 of SEQ ID NO: 14;

and wherein the variant has alpha-amylase activity.

Without wishing to be bound by theory, the applicant believes that the stability of alpha-amylases when used in starch processing is negatively affected by spontaneous Maillard reactions taking place between a reducing sugar like glucose and a free amino group present on either the amino terminal of a polypeptide or the side chains of arginines and lysines. The reaction rate is increasing as the temperature increases. Lysine residues are more reactive than arginine residues and the N-terminal amino group. The initial Maillard reaction between a sugar and e.g. the amino group at the end of a lysine side chain can continue into a cascade of secondary reactions, but they all lead to a modified lysine residues that may have lost its function in the context of the enzyme, with effects on stability and/or activity. Hence, it is believed that a variant of a parent alpha-amylase, such as a parent alpha-amylase, which has at least 80% sequence identity to (i) the mature polypeptide of any of SEQ ID NO: 14, or (ii) amino acids 1 to 481 of SEQ ID NO: 14, in which a lysine is substituted to a non-native amino acid, has improved stability in the presence of glucose as compared to the parent.

The alpha-amylase may be of any origin, such as bacterial origin, especially *Bacillus* origin, such as *Bacillus licheniformis* origin.

In a preferred embodiment the alpha-amylase variant comprises or has the following or corresponding group a) and group b) substitutions:
group a): K176L+E185P+I201Y+H205Y+K213T+Q360S+D416V+R437W; and one or more of the following substitutions in group b): K136, K154, K170, K234, K237, K251, K315, K319, K392 (using SEQ ID NO: 1 for numbering).

In a further preferred embodiment, the alpha-amylase variant comprises or has one or more substitutions, using SEQ ID NO: 1 for numbering, or corresponding substitutions, in groups a) and b):
  group a) K176, E185, I201, H205, K213, Q360, D416, R437;
  group b) K136, K154, K170, K234, K237, K251, K306, K315, K319, K392; wherein
  the variant has at least 80%, but less than 100% sequence identity to:
  (i) the mature polypeptide of any of SEQ ID NOs: 1 or 14, or
    amino acids 1 to 483 of SEQ ID NO: 1 or amino acids 1 to 481 of SEQ ID NO: 14;
    and wherein the variant has alpha-amylase activity.

In a preferred embodiment the alpha-amylase variant comprises or has the following or corresponding group a) and group b) substitutions:
group a): K176L+E185P+I201Y+H205Y+K213T+Q360S+D416V+R437W; and one or more of the following substitutions in group b): K136R, K154A, K154H, K154S, K170R, K170S, K234T, K237R, K251Q, K315M, K319Q, K319L, K392V (using SEQ ID NO: 1 for numbering).

In other preferred embodiments the variant comprises or has the following or corresponding group a) and group b) substitutions:
  group a): K176L+E185P+I201Y+H205Y+K213T+Q360S+D416V+R437W; or
  K176L+I201Y+H205Y+K213T+E255P+Q360S+D416V+R437W and
one or more of the following substitutions in group b):
  K136, K154, K170, K234, K237, K251, K306, K315, K319, K392 (using SEQ ID NO: 1 for numbering).

In an embodiment the group b) substitution is K136R (using SEQ ID NO: 1 for numbering). In an embodiment the group b) substitution is K154A, H, S (using SEQ ID NO: 1 for numbering). In an embodiment the group b) substitution is K170R, S (using SEQ ID NO: 1 for numbering). In an embodiment the group b) substitution is K234T (using SEQ ID NO: 1 for numbering). In an embodiment the group b) substitution is K237R (using SEQ ID NO: 1 for numbering). In an embodiment the group b) substitution is K251Q (using SEQ ID NO: 1 for numbering). In an embodiment the group b) substitution is K315A, N, C, Q, E, G, H, I, L, M, F, P, S, T, W, Y, V (using SEQ ID NO: 1 for numbering). In an embodiment the group b) substitution is K319Q, L (using SEQ ID NO: 1 for numbering). In an embodiment the group b) substitution is K392V (using SEQ ID NO: 1 for numbering). In an embodiment the group b) substitutions are selected from the group consisting of:
K136R;
K154A;
K154H;
K154S;
K170R;
K170S;
K234T;
K237R;
K251Q;
K306M
K315M;
K319Q;
K319L;
K392V;
K392V+Q393D;
H133Y+K136R (using SEQ ID NO: 1 for numbering).

In an embodiment the variant of the invention further includes a substitution in any of positions H68, H133, H142, Y156, Y158, H316, L318 using SEQ ID NO: 1 for numbering. In a preferred embodiment the substitution is one or more of the following substitutions: H68W, H133Y, H142Y, Y156W, Y158W, H316W, L318W.

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): K316R (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): K154A, H, S (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): K170R, S (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): K234T (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): K237R (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
  group b): K306M or K251Q (using SEQ ID NO: 1 for numbering). In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and group b): K315A, N, C, Q, E, G, H, I, L, M, F, P, S, T, W, Y, V (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): K315M (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): K319Q, L (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): K392V (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): K392V+Q393D (using SEQ ID NO: 1 for numbering).

In a preferred embodiment the variant of the invention comprises or has the following group a) and group b) substitutions or corresponding substitutions in other parent alpha-amylases:
group a): K176L+E185P+I201Y+H205Y+K213T+Q360S+D416V+R437W; and
group b): H133Y+K136R (using SEQ ID NO: 1 for numbering).

In an embodiment the variant of the invention has at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of any of SEQ ID NO: 1, or (ii) amino acids 1 to 483 of SEQ ID NO: 1.

According to the invention the variant is a variant of a parent alpha-amylase, which parent alpha-amylase has at least 85%, at least 90%, at least 95%, at least 96%, at least 97%, at least 98%, at least 99% or 100% sequence identity to (i) the mature polypeptide of any of SEQ ID NO: 1, or (ii) amino acids 1 to 483 of SEQ ID NO: 1.

In another embodiment the variant of the invention comprises or has the following or corresponding group a) and group b) substitutions:
group a): K174L+E183P+F199Y+H203Y+K211+Q358S+D414V+R435W; and one or more of the following substitutions in group b): K134, K152, K168, K232, K235, K249, K313, K317, K390 (using SEQ ID NO: 14 for numbering).

In a further embodiment, the variant comprises or has the following or corresponding group a) and group b) substitutions:
group a): K174L+E183P+F199Y+H203Y+K211+Q358S+D414V+R435W; or
K174L+F199Y+H203Y+K211 T+E253P+Q358S+D414V+R435W and
one or more of the following substitutions in group b): K134, K152, K168, K232, K235, K249, K304M, K313, K317, K390 (using SEQ ID NO: 14 for numbering).

In an embodiment the group b) substitution is K134R (using SEQ ID NO: 14 for numbering). In an embodiment the group b) substitution is K152A, H, S (using SEQ ID NO: 14 for numbering). In an embodiment the group b) substitution is K168R, S (using SEQ ID NO: 14 for numbering). In an embodiment the group b) substitution is K232T (using SEQ ID NO: 14 for numbering). In an embodiment the group b) substitution is K235R (using SEQ ID NO: 14 for numbering). In an embodiment the group b) substitution is K249Q (using SEQ ID NO: 14 for numbering). In an embodiment the group b) substitution is K313A, N, C, Q, E, G, H, I, L, M, F, P, S, T, W, Y, V (using SEQ ID NO: 14 for numbering). In an embodiment the group b) substitution is K317Q, L (using SEQ ID NO: 14 for numbering). In an embodiment the group b) substitution is K390V (using SEQ ID NO: 14 for numbering).

In a preferred embodiment the group b) substitutions are selected from the group consisting of:
K134R;
K152A;
K152H;
K152S;
K168R;
K168S;
K232T;
K235R;
K249Q;
K304M
K313M;
K317Q;
K317L;
K390V;
K390V+Q391 D;
H131Y+K134R (using SEQ ID NO: 14 for numbering).

In an embodiment the variant of the invention further includes a substitution in any of positions H66, H131, H140, Y154, Y156, H314, L316 using SEQ ID NO: 14 for numbering. In a preferred embodiment the substitution is one or more of the following substitutions: H66W, H131Y, H140Y, Y154W, Y156W, H314W, L316W.

In a preferred embodiment the variant of the invention comprises or has the following group a) and group b) substitutions or corresponding substitutions in other parent alpha-amylases:
group a): K174L+E183P+F199Y+H203Y+K211T+Q358S+D414V+R435W; and
group b): K134R (using SEQ ID NO: 14 for numbering).

In a preferred embodiment the variant of the invention comprises or has the following group a) and group b) substitutions or corresponding substitutions in other parent alpha-amylases:
group a): K174L+E183P+F199Y+H203Y+K211T+Q358S+D414V+R435W; and
group b): K152A, H, S (using SEQ ID NO: 14 for numbering).

In a preferred embodiment the variant of the invention comprises or has the following group a) and group b) substitutions or corresponding substitutions in other parent alpha-amylases:
group a): K174L+E183P+F199Y+H203Y+K211T+Q358S+D414V+R435W; and
group b): K168R, S (using SEQ ID NO: 14 for numbering).

In a preferred embodiment the variant of the invention comprises or has the following group a) and group b) substitutions or corresponding substitutions in other parent alpha-amylases:

group a): K174L+E183P+F199Y+H203Y+K211T+Q358S+ D414V+R435W; and
group b): K232T (using SEQ ID NO: 14 for numbering).

In a preferred embodiment the variant of the invention comprises or has the following group a) and group b) substitutions or corresponding substitutions in other parent alpha-amylases:
group a): K174L+E183P+F199Y+H203Y+K211T+Q358S+ D414V+R435W; and
group b): K235R (using SEQ ID NO: 14 for numbering).

In a preferred embodiment the variant of the invention comprises or has the following group a) and group b) substitutions or corresponding substitutions in other parent alpha-amylases:
group a): K174L+E183P+F199Y+H203Y+K211T+Q358S+ D414V+R435W; and
group b): K249Q (using SEQ ID NO: 14 for numbering).

In a preferred embodiment the variant of the invention comprises or has the following group a) and group b) substitutions or corresponding substitutions in other parent alpha-amylases:
group a): K174L+E183P+F199Y+H203Y+K211T+Q358S+ D414V+R435W; and
group b): K313A, N, C, Q, E, G, H, I, L, M, F, P, S, T, W, Y, V (using SEQ ID NO: 14 for numbering).

In a preferred embodiment the variant of the invention comprises or has the following group a) and group b) substitutions or corresponding substitutions in other parent alpha-amylases:
group a): K174L+E183P+F199Y+H203Y+K211T+Q358S+ D414V+R435W; and
group b): K313M (using SEQ ID NO: 14 for numbering).

In a preferred embodiment the variant of the invention comprises or has the following group a) and group b) substitutions or corresponding substitutions in other parent alpha-amylases:
group a): K174L+E183P+F199Y+H203Y+K211T+Q358S+ D414V+R435W; and
group b): K317Q, L (using SEQ ID NO: 14 for numbering).

In a preferred embodiment the variant of the invention comprises or has the following group a) and group b) substitutions or corresponding substitutions in other parent alpha-amylases:
group a): K174L+E183P+F199Y+H203Y+K211T+Q358S+ D414V+R435W; and
group b): K390V (using SEQ ID NO: 14 for numbering).

In a preferred embodiment the variant of the invention has at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 14, or (ii) amino acids 1-481 of SEQ ID NO: 14.

According to the invention the variant is a variant of a parent alpha-amylase, which parent alpha-amylase has at least 80%, at least 85%, at least 90%, at least 95%, at least 96%, at least 97%, at least 98%, at least 99% or 100% sequence identity to (i) the mature polypeptide of any of SEQ ID NO: 14, or (ii) amino acids 1 to 481 of SEQ ID NO: 14.

In one embodiment, the total number of substitutions in the variants of the present invention is 2-30, e.g., 2-25 or 2-20 or 9-30, such as 9-25, such as 2, 3, 4, 5, 6, 7, 8, 9, 10, 11, 12, 13, 14, 15, 16, 17, 18, 19, 20, 21, 22, 23, 24, 25, 26, 27, 28, 29 or 30 substitutions Improved Stability and/or Activity Ratio A variant of the invention has improved stability, in particular improved stability in the presence of glucose compared to the mature polypeptide of SEQ ID NO: 1 or 14, respectively.

In particular embodiments, the variant has at least 80%, such as at least 85%, at least 90%, at least 91%, at least 92%, at least 93%, at least 94%, at least 95%, at least 96%, at least 97%, at least 98% or at least 99%, but less than 100% sequence identity to the mature polypeptide of any of SEQ ID NO: 1 and has improved stability, in particular improved stability in the presence of glucose, compared to the mature polypeptide of SEQ ID NO: 1.

Further embodiments provide a variant, which has at least 80%, such as at least 85%, at least 90%, at least 91%, at least 92%, at least 93%, at least 94%, at least 95%, at least 96%, at least 97%, at least 98% or at least 99%, but less than 100% sequence identity to amino acids 1 to 483 of SEQ ID NO: 1 and has improved stability, in particular improved stability in the presence of glucose, compared to amino acids 1 to 483 of SEQ ID NO: 1.

Other embodiments provide a variant, which has at least 80%, such as at least 85%, at least 90%, at least 91%, at least 92%, at least 93%, at least 94%, at least 95%, at least 96%, at least 97%, at least 98% or at least 99%, but less than 100% sequence identity to the mature polypeptide of any of SEQ ID NO: 1 and has improved stability, in particular improved stability in the presence of glucose, compared to the mature polypeptide of SEQ ID NO: 14.

In even further embodiments, the variant has at least 80%, such as at least 85%, at least 90%, at least 91%, at least 92%, at least 93%, at least 94%, at least 95%, at least 96%, at least 97%, at least 98% or at least 99%, but less than 100% sequence identity to amino acids 1 to 483 of SEQ ID NO: 1 and has improved stability, in particular improved stability in the presence of glucose, compared to amino acids 1 to 481 of SEQ ID NO: 14.

The stability of the variant may be determined by calculating the residual activity as the ratio between the alpha-amylase activity present after incubation of said variant with 10% (w/w) glucose for 6 hours at 60° C. to the activity present after incubation of said variant with 10% (w/w) glucose for 6 hours at 4° C.

It is well within the capacity of a skilled person to determine alpha-amylase activity, for instance by using the protocols described herein using the Phadebas substrate (from for example Magle Life Sciences, Lund, Sweden) using the protocol described in the materials and methods sections herein. Similar protocols can be used with the Amylazym™ substrate from Megazyme, Inc., Ireland.

According to some embodiments the invention provides a variant, wherein the stability of said variant when determined as the ratio between the alpha-amylase activity present after incubation of the variant with 10% (w/w) glucose for 6 hours at 60° C. to the activity present after incubation of the variant with 10% (w/w) glucose for 6 hours at 4° C. is at least 35%, such as at least 36%, 37%, 38%, 39%, 40%, 41%, 42%, 43%, 44%, 45%, 46%, 47%, 48%, 49%, 50%, 55%, 60%, 65%, 70%, 75% or at least 80%. A variant of the invention has a relatively higher activity on long chain versus short chain substrates as compared to the mature polypeptide of SEQ ID NO: 1 or 14, respectively.

Additional Substitutions

The variants of the invention may further comprise one or more (e.g., several) additional alterations, e.g., one or more (e.g., several) additional substitutions.

The additional amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

The variants may consist of 300 to 500, e.g., 350 to 495, 400 to 490, 450 to 485 amino acids.

Parent Alpha-Amylase

The variant is preferably a variant of a parent alpha-amylase selected from the group consisting of:
(a) a polypeptide having at least 80% sequence identity to (i) the mature polypeptide of any of SEQ ID NOs: 1 or 2, or (ii) amino acids 1 to 483 of SEQ ID NO: 1, or amino acids 1 to 481 of SEQ ID NO: 14; or
(b) a fragment of the mature polypeptide of any of SEQ ID NOs: 1 or 14, which has alpha-amylase activity.

In one embodiment, the parent alpha-amylase has at least 80%, at least 85%, at least 90%, at least 95%, at least 96%, at least 97%, at least 98%, at least 99% or 100% sequence identity to (i) the mature polypeptide of any of SEQ ID NOs: 1 or 2, or (ii) amino acids 1 to 483 of SEQ ID NO: 1 or amino acids 1 to 481 of SEQ ID NO: 14.

In one embodiment, the parent alpha-amylase comprises or consists of the mature polypeptide of any of SEQ ID NOs: 1 or 14.

In another embodiment, the parent alpha-amylase is a fragment of the mature polypeptide of any of SEQ ID NOs: 1 or 14, wherein the fragment has alpha-amylase activity.

The parent may be a hybrid polypeptide in which a region of one polypeptide is fused at the N-terminus or the C-terminus of a region of another polypeptide.

For instance, the parent alpha-amylase shown in SEQ ID NO: 14 (LE399) is a hybrid polypeptide, which has previously been disclosed in, e.g., WO 2002/010355). SEQ ID NO: 14 (LE399) comprises amino acids 1-37 of the alpha-amylase from Bacillus amyloliquefaciens (SEQ ID NO: 6) and amino acids 40-483 of the alpha-amylase from Bacillus licheniformis (SEQ ID NO: 1) with the following substitutions G48A+T491+G107A+H156Y+A181T+N190F+I201F+A209V+Q264S (using SEQ ID NO: 1 for numbering).

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial alpha-amylase. For example, the parent may be a Gram-positive bacterial polypeptide such as a Bacillus, Clostridium, Enterococcus, Geobacillus, Lactobacillus, Lactococcus, Oceanobacillus, Staphylococcus, Streptococcus, or Streptomyces alpha-amylase, or a Gram-negative bacterial polypeptide such as a Campylobacter, E. coli, Flavobacterium, Fusobacterium, Helicobacter, Ilyobacter, Neisseria, Pseudomonas, Salmonella, or Ureaplasma alpha-amylase.

In one aspect, the parent is a Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, or Bacillus thuringiensis alpha-amylase.

In an preferred embodiment the parent is a *Bacillus licheniformis* alpha-amylase.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having alpha-amylase activity, comprising:

(a) introducing into a parent alpha-amylase one or more substitutions, using SEQ ID NO: 1 for numbering, or corresponding substitutions, in groups a) and b):

group a) K176, E185, I201, H205, K213, Q360, D416, R437;

group b) K136, K154, K170, K234, K237, K251, K315, K319, K392; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis alkaline* protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "*Yeast*" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of *Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. *Yeast* may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising an alpha-amylase variant and at least one additional enzyme. The additional enzyme(s) may be selected from the group consisting of beta-amylase, cellulase (beta-glucosidase, cellobiohydrolase and endoglucanase), glucoamylase, hemicellulsae (e.g., xylanase), isoamylase, isomerase, lipase, phytase, protease, pullulanase, and/or other enzymes useful in a commercial process in conjunction with an alpha-amylase.

The additional enzyme may also be a second alpha-amylase. Such enzymes are known in the art in starch processing, sugar conversion, fermentations for alcohol and other useful end-products, commercial detergents and cleaning aids, stain removal, fabric treatment or desizing, and the like.

In an embodiment the additional alpha-amylase may be an alpha-amylase of another origin. When the alpha-amylase variant of the invention is of the parent alpha-amylase shown in SEQ ID NO: 1 (i.e., *Bacillus licheniformis* alpha-amylase) the additional alpha-amylase may be a *Bacillus stearothermophilus* alpha-amylase, such as the mature part of the alpha-amylase disclosed in WO 2002/010355 as SEQ ID NO: 6, or a variant thereof.

When the alpha-amylase variant of the invention is the parent alpha-amylase shown in SEQ ID NO: 14 (i.e., hybrid alpha-amylase of *Bacillus amyloliquefaciens* alpha-amylase shown in SEQ ID NO: 6 and a variant of the *Bacillus licheniformis* alpha-amylase shown in SEQ ID NO: 1 or LE399) the additional/second alpha-amylase may be a *Bacillus stearothermophilus* alpha-amylase, such as the mature part of the alpha-amylase disclosed in WO 2002/010355 as SEQ ID NO: 6, or a variant thereof.

USES

The variants of the present invention possess valuable properties allowing for a variety of industrial applications. The alpha-amylase variants may be used for starch processes, in particular starch conversion, especially liquefaction of starch (see, e.g., U.S. Pat. No. 3,912,590, EP 252730 and EP 063909, WO 99/19467, and WO 96/28567, which are all hereby incorporated by reference). Also contemplated are compositions for starch conversion purposes, which may beside the variant of the invention also comprise an glucoamylase, pullulanase, and other alpha-amylases.

A variant of the invention is particularly useful in the production of sugars (including sweeteners and syrups) and ethanol (see, e.g., U.S. Pat. No. 5,231,017, which is hereby incorporated by reference), such as fuel, drinking and industrial ethanol, from starch or whole grains.

The variants of the invention may also be used in detergents, in particular laundry detergent compositions and dishwashing detergent compositions, hard surface cleaning compositions, and for desizing textiles, fabrics or garments, production of pulp and paper, beer making, ethanol production, and starch conversion processes.

The variants may also be used for desizing of textiles, fabrics, and garments (see, e.g., WO 95/21247, U.S. Pat. No. 4,643,736, and EP 119920, which are incorporated herein by reference), beer making or brewing, and in pulp and paper production or related processes.

Starch Processing

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be suitably processed. This reduction in viscosity is primarily attained by enzymatic degradation in current commercial practice.

Conventional starch-conversion processes, such as liquefaction and saccharification processes are described in a vast number of documents including U.S. Pat. No. 3,912,590, EP 252730, EP 063909, and WO 2002/010355, which are incorporated herein by reference.

In an embodiment, the conversion process, degrading starch to lower molecular weight carbohydrate components such as sugars or fat replacers, includes a debranching step.

In the case of converting starch into sugars, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup dextrose syrup may be converted into fructose. After saccharification of liquefied mash, the dextrose syrup is converted into high fructose syrup using, e.g., an immobilized glucose isomerase.

In one aspect, the invention relates to processes of producing sugars, comprising (a) liquefying a starch-containing material with an alpha-amylase variant of the invention to produce a liquefied mash;

(b) saccharifying the liquefied mash to produce fermentable sugars.

The sugars are optionally recovered and/or further processes to, e.g., high fructose syrup, as described above, e.g., using an immobilized glucose isomerase.

Process conditions are well know by the skilled person in the art. Suitable starch-containing starting materials are listed in the section "Starch-Containing Materials"-section below. In an embodiment the starch-containing materials is corn or wheat. Contemplated enzymes are listed in the "Enzymes"-section below. The liquefaction is carried out in the presence of an alpha-amylase variant of the invention or composition of the invention.

The temperature during liquefaction step (a) is above the initial gelatinization temperature, such as from 70-120° C., preferably 80-100° C., especially between 80-90° C., such as around 85° C.

In an embodiment step (a) is performed at pH 4-6, preferably 4.2-5.5, such as around 4.5. In an embodiment liquefaction in step (a) is carried out for 0.1-12 hours, such as 0.5-5 hours. In an embodiment the temperature during step (b) or pre-saccharification is in the range from 30-70° C., such as 55-65° C., typically around 60° C. Saccharification step (b) is typically done using a carbohydrate-source generating enzyme, such as a glucoamylase. The sugars obtained from saccharification step (b) may be recovered and/or may be further processes to, e.g., high fructose syrup, such as HFCS, e.g., using an immobilized glucose isomerase.

Processes for Producing Fermentation Products from Gelatinized Starch-Containing Material In this aspect the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying a starch-containing material with an alpha-amylase variant of the invention to produce a liquefied mash;

(b) saccharifying the liquefied mash to produce fermentable sugars; and (c) fermenting the fermentable sugars using a fermenting organism.

The fermentation product, such as especially ethanol, may optionally be recovered after fermentation, e.g., by distillation. Suitable starch-containing starting materials are listed in the section "Starch-Containing Materials"-section below. In an embodiment the starch-containing materials is corn or wheat. Contemplated enzymes are listed in the "Enzymes"-section below. The liquefaction is carried out in the presence of an alpha-amylase variant of the invention or composition of the invention.

The fermenting organism is preferably yeast, preferably a strain of *Saccharomyces*, especially a strain of *Saccharomy-* ces cerevisae. Suitable fermenting organisms are listed in the "Fermenting Organisms"-section below. In a preferred embodiment steps (b) and (c) are carried out sequentially or simultaneously (i.e., as SSF process). In a particular embodiment, the process of the invention further comprises, prior to liquefaction step i), the steps of:
 x) reducing the particle size of the starch-containing material, preferably by milling;
 y) forming a slurry comprising the starch-containing material and water.

The aqueous slurry may contain from 10-55 wt.-% dry solids, preferably 25-45 wt.-% dry solids, more preferably 30-40 wt.-% dry solids of starch-containing material. The slurry is heated to above the initial gelatinization temperature. An alpha-amylase variant of the invention, or composition of the invention, may be added to the slurry. In an embodiment the slurry is also jet-cooked to further gelatinize the slurry before being subjected to an alpha-amylase variant of the invention in liquefaction step (a).

The temperature during liquefaction step (a) is above the initial gelatinization temperature, such as from 70-120° C., preferably 80-100° C., especially between 80-90° C., such as around 85° C.

In an embodiment liquefaction is carried out as a three-step hot slurry process. The slurry is heated to between 60-95° C., preferably between 80-90° C., such as around 85° C., and an alpha-amylase variant of the invention is added to initiate liquefaction (thinning). Then the slurry is jet-cooked at a temperature between 95-140° C., preferably 105-125° C., for 1-15 minutes, preferably for 3-10 minutes, especially around 5 minutes. The slurry is cooled to 60-95° C., preferably 80-90° C., and more alpha-amylase is added to finalize hydrolysis (secondary liquefaction). The liquefaction process is usually carried out at pH 4-6, preferably 4.2-5.5, such as around 4.5. Milled and liquefied starch is known as "mash".

Saccharification in step (b) may be carried out using conditions well known in the art. Saccharification is typically carried out at temperatures from 30-70° C., such as 55-65° C., typically around 60° C., at a pH between 4 and 5, normally at about pH 4.5.

For instance, a full saccharification process may last up to from about 24 to about 72 hours.

In an embodiment a pre-saccharification step is done at 40-90 minutes at a temperature between 30-70° C., such as 55-65° C. typically at about 60° C., followed by complete saccharification during fermentation in a simultaneous saccharification and fermentation step (SSF).

The most widely used process in fermentation product production, especially ethanol production, is simultaneous saccharification and fermentation (SSF) process, in which there is no holding stage for the saccharification. SSF may typically be carried out at a temperature between 25° C. and 40° C., such as between 28° C. and 36° C., such as between 30° C. and 34° C., such as around 32° C., especially then the fermentation organism is yeast, such as a strain of Saccharomyces cerevisiae, and the desired fermentation product is ethanol.

In an embodiment fermentation is ongoing for 6 to 120 hours, in particular 24 to 96 hours.

Other fermentation products may be fermented at conditions and temperatures, well known to the skilled person in the art, suitable for the fermenting organism in question. According to the invention the temperature may be adjusted up or down during fermentation.

In an embodiment a protease is adding during fermentation. Examples of proteases can be found in the "Proteases"-section below.

Starch-Containing Materials

According to the invention any suitable starch-containing starting material may be used according to the present invention. The starting material is generally selected based on the desired fermentation product. Examples of starch-containing starting materials, suitable for use in a process of present invention, include whole grains, corns, wheat, barley, rye, milo, sago, cassava, tapioca, sorghum, rice, peas, beans, and sweet potatoes, or mixtures thereof, or cereals, or sugar-containing raw materials, such as molasses, fruit materials, sugar cane or sugar beet, potatoes. Contemplated are both waxy and non-waxy types of corn and barley.

The raw material, such as whole grain, is milled in order to open up the structure and allowing for further processing. Two milling processes are preferred according to the invention: wet and dry milling. In dry milling whole kernels are milled and used. Wet milling gives a good separation of germ and meal (starch granules and protein) and is often applied at locations where the starch hydrolyzate is used in production of syrups. Both dry and wet milling is well known in the art of starch processing and is equally contemplated for the process of the invention.

Fermenting Organisms

The term "fermenting organism" refers to any organism, including bacterial and fungal organisms, including yeast and filamentous fungi, suitable for producing a desired fermentation product. Especially suitable fermenting organisms according to the invention are able to ferment, i.e., convert sugars, such as glucose, fructose, maltose, directly or indirectly into the desired fermentation product. Examples of fermenting organisms include fungal organisms, such as yeast. Preferred yeast includes strains of the genus Saccharomyces, in particular a strain of Saccharomyces cerevisiae or Saccharomyces uvarum.

In one embodiment the fermenting organism is added in fermentation so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Fermentation Products

The term "fermentation product" means a product produced in a process including a fermentation step using a fermenting organism. Fermentation products contemplated according to the invention include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones.

In a preferred embodiment the fermentation product is ethanol, e.g., fuel ethanol; drinking ethanol, i.e., potable neutral spirits; or industrial ethanol.

Low-Temperature Processes for Hydrolysis of Starch

As is apparent, in the above-described traditional glucose processing, a starch slurry is subjected to primary and secondary liquefaction comprising a pH adjustment and a steam jetting treatment at pH 5.5, 105° C. for 0.1 hr, followed by treatment at 95° C. for 1-2 hours. This is traditionally followed by a step of cooling to 60° C. and pH adjustment to pH 4.0-4.5 for 30-60 hours for a separate saccharification step. Thus, the traditional process requires separate liquefaction and saccharification steps, as well as energy and chemical costs.

In addition, the present invention also includes use of the alpha-amylase variants in starch hydrolysis processes comprising for a single, lower temperature process, which can reduce energy and chemical costs due to, e.g., lower steam use at lower temperatures, and lower chemical use for pH adjustment, as well as other benefits. Such processes of the present invention can eliminate the need for a separate primary and secondary liquefaction step, as well as a separate carbon column filtration required in traditional processing.

Such processes can also provide a high degree of starch solubilisation, result in high purity dextrose syrup, and can decrease hydrolysis time for an overall decrease in total processing time. Additional benefits can include lower Maillard products and protein solubilisation in syrup.

These process involve activity toward raw starch at a temperature below or just above the initial gelatinization temperature of starch, e.g., 60-70° C., such as 60-66° C., which is particularly relevant for corn starch. The activity toward raw starch is shown by increasing starch solubilisation at low temperature.

In an aspect a one step process for producing a soluble starch hydrolysate is contemplated, the process comprising subjecting an aqueous granular starch slurry at a temperature below or just above the initial gelatinization temperature of said granular starch to the action of an alpha-amylase variant as described herein.

In a further aspect the process is for production of high fructose starch-based syrup (HFSS), the process comprising producing a soluble starch hydrolysate by the process of the preceding aspect of the invention, and further comprising a step for conversion of the soluble starch hydrolysate into high fructose starch-based syrup (HFSS). In some embodiments, dextrose syrup can be produced while starch is being hydrolysed, i.e., in a single step or nearly simultaneous process along with addition of the alpha-amylase variant.

In a further aspect the process is for production of maltose syrup, the process comprising producing a soluble starch hydrolysate by the process of a preceding aspect of the invention, and further comprising a step for conversion of the soluble starch hydrolysate into maltose syrup. In some embodiments, maltose syrup can be produced while starch is being hydrolysed, i.e., in a single step or nearly simultaneous process along with addition of the alpha-amylase variant.

For example, maltose syrup can be prepared from a 5-20 DE partially hydrolysed starch substrate by saccharification using a maltose-producing enzyme at temperature 50-60° C. and pH 5. Maltogenic enzymes such as beta-amylase extracted from germinated barley, or microbial beta-amylase or fungal alpha amylase derived from *Aspergillus oryzae* are used to produce a hydrolyzate containing about 40-55 wt % maltose. Higher levels of maltose i.e. 55-85 wt % are produced by saccharification using a combination of a beta-amylase, a maltogenic anzyme and a debranching enzyme such as a pullulanase. In some embodiments, high conversion syrups of 60-70 DE containing intermediate levels of maltose and dextrose are also produced.

The starch slurry to be subjected to the processes of the invention may have 20-55% dry solids granular starch, preferably 25-40% dry solids granular starch, more preferably 30-35% dry solids granular starch.

After being subjected to such processes at least 85%, 86%, 87%, 88%, 89%, 90%, 91%, 92%, 93%, 94%, 95%, 96%, 97%, 98%, or preferably 99% of the dry solids of the granular starch is converted into a soluble starch hydrolysate.

The processes are conducted at a temperature below the initial gelatinization temperature. In such embodiment, the temperature at which the processes are conducted is at least 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., or preferably at least 60° C.

The processes are conducted at a temperature below or just above the initial gelatinization temperature of starch. In a particular embodiment, the process is performed at a temperature of about 60-70° C., such as about 60-66° C., and in particular at about 60° C., about 61° C., about 62° C., about 63° C., about 64° C., about 65° C. and/or about 66° C. These temperature ranges are particularly relevant where the starch is corn starch. As mentioned, one of skill in the art will recognize that various starches will have an initial gelatinization temperature that may vary according to the plant species, the particular variety of plant species, and/or to the growth conditions, and the temperature conditions can be adjusted accordingly.

The pH at which the processes are conducted may in be in the range of 3.0 to 7.0, preferably from 3.5 to 6.0, or more preferably from 4.0-5.0, or preferably from 4.5-5.5, such as about 4.5.

The exact composition of the soluble starch hydrolysate produced depends on the combination of enzymes applied as well as the type of granular starch processed. Preferably the soluble hydrolysate is maltose with a purity of at least 85%, 90%, 95.0%, 95.5%, 96.0%, 96.5%, 97.0%, 97.5%, 98.0%, 98.5&, 99.0% or 99.5%. Even more preferably the soluble starch hydrolysate is glucose, and most preferably the starch hydrolysate has a DX (glucose percent of total solubilised dry solids) of at least 85%, 90%, 91.0%, 91.5%, 92.0%, 92.5%, 93.0%, 93.5%, 94.0%, 94.5%, 95.0%, 95.5%, 96.0%, 96.5%, 97.0%, 97.5%, 98.0%, 98.5, 99.0% or 99.5%. Equally contemplated, however, is the process wherein the product of the process of the invention, the soluble starch hydrolysate, is a speciality syrup, such as a speciality syrup containing a mixture of glucose, maltose (DP2), DP3 and DPn for use in the manufacture of ice creams, cakes, candies, canned fruit.

Beer Making

An alpha-amylase variant of the invention may also be used in a beer-making process and similar fermentations. Alpha-amylase is typically added during the mashing process. The process is substantially similar to the milling, liquefaction, saccharification, and fermentation processes described above.

Pulp and Paper Production

An alpha-amylase variant of the invention may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase variants are especially useful in a process for producing a papermaking pulp from starch-coated printed-paper. The process may be performed as described in WO 95/14807, comprising the following steps:

a) disintegrating the paper to produce a pulp, b) treating with a starch-degrading enzyme before, during or after step a), and c) separating ink particles from the pulp after steps a) and b).

The alpha-amylase variants may also be useful in modifying starch where enzymatically modified starch is used in papermaking together with alkaline fillers such as calcium carbonate, kaolin and clays. With the alpha-amylase variants it is possible to modify the starch in the presence of the filler thus allowing for a simpler integrated process.

Desizing of Textiles, Fabrics and Garments

An alpha-amylase variant of the invention may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing process is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size leads to some fiber damage because of the rather aggressive chemicals used. The alpha-amylase variants may be used alone or in combination with a cellulase when desizing cellulose-containing fabric or textile.

Desizing and bleaching processes are well known in the art. For instance, such processes are described in e.g., WO 95/21247, U.S. Pat. No. 4,643,736, EP 119920, which are hereby incorporated by reference.

Cleaning Processes and Detergent Compositions

An alpha-amylase variant of the invention may be added as a component of a detergent composition for various cleaning or washing processes, including laundry and dishwashing. For example, the variants may be used in the detergent compositions described in WO 96/23874 and WO 97/07202.

The alpha-amylase variants may be incorporated in detergents at conventionally employed concentrations. For example, a variant of the invention may be incorporated in an amount corresponding to 0.00001-10 mg (calculated as pure, active enzyme protein) of alpha-amylase per liter of wash/dishwash liquor using conventional dosing levels of detergent.

The detergent composition may for example be formulated as a hand or machine laundry detergent composition, including a laundry additive composition suitable for pretreatment of stained fabrics and a rinse added fabric softener composition or be formulated as a detergent composition for use in general household hard surface cleaning operations, or be formulated for hand or machine dishwashing operations.

The detergent composition may further comprise one or more other enzymes, such as a lipase, peroxidase, protease, another amylolytic enzyme, e.g., another alpha-amylase, glucoamylase, maltogenic amylase, CGTase, cellulase, mannanase (such as Mannaway™ from Novozymes, Denmark), pectinase, pectin lyase, pectate lyase (such as XPect™ from Novozymes A/S, Denmark), cutinase, and/or laccase.

In general the properties of the chosen enzyme(s) should be compatible with the selected detergent (i.e., pH-optimum, compatibility with other enzymatic and non-enzymatic ingredients, etc.), and the enzyme(s) should be present in effective amounts.

The detergent enzyme(s) may be included in a detergent composition by adding separate additives containing one or more enzymes, or by adding a combined additive comprising all of these enzymes. A detergent additive, e.g., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols, fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition may be in any convenient form, e.g., a bar, a tablet, a powder, a granule, a paste or a liquid. A liquid detergent may be aqueous, typically containing up to about 70% water and 0 to about 30% organic solvent, or non-aqueous.

The detergent composition comprises one or more surfactants, which may be non-ionic including semi-polar and/or anionic and/or cationic and/or zwitterionic. The surfactants are typically present at a level of from about 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0 to about 65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinyl-pyrrolidone), poly (ethylene glycol), poly(vinyl alcohol), poly (vinylpyridine-N-oxide), poly(vinylimidazole), polycarboxylates such as polyacrylates, maleiclacrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxyben-zenesul-fonate. Alternatively, the bleaching system may comprise peroxy acids of, e.g., the amide, imide, or sulfone type.

The enzyme(s) of the detergent composition may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19708 and WO 92/19709.

The detergent may also contain other conventional detergent ingredients such as, e.g., fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

The detergent compositions may comprise any enzyme in an amount corresponding to 0.01-100 mg of enzyme protein per liter of wash liquor, preferably 0.055 mg of enzyme protein per liter of wash liquor, in particular 0.1-1 mg of enzyme protein per liter of wash liquor.

One or more of the variant enzymes described herein may additionally be incorporated in the detergent formulations disclosed in WO 97/07202, which is hereby incorporated as reference.

Embodiments of the Invention

1. An alpha-amylase variant of a parent alpha-amylase comprising one or more substitutions, using SEQ ID NO: 1 for numbering, or corresponding substitutions, in groups a) and b):
group a) K176, E185, I201, H205, K213, Q360, D416, R437;
group b) substitution of an additional lysine residue to a non-native amino acid;
wherein the variant has at least 80%, but less than 100% sequence identity to:
(i) the mature polypeptide of any of SEQ ID NOs: 1 or 14, or
(ii) amino acids 1 to 483 of SEQ ID NO: 1 or amino acids 1 to 481 of SEQ ID NO: 14; and wherein the variant has alpha-amylase activity.
2. An alpha-amylase variant of a parent alpha-amylase comprising one or more substitutions, using SEQ ID NO: 1 for numbering, in groups a) and b):
group a) K176, E185, I201, H205, K213, Q360, D416, R437;
group b) K136, K154, K170, K234, K237, K251, K306, K315, K319, K392;
wherein the variant has at least 80%, but less than 100% sequence identity to:
(ii) the mature polypeptide of any of SEQ ID NOs: 1 or 14, or amino acids 1 to 483 of SEQ ID NO: 1 or amino acids 1 to 481 of SEQ ID NO: 14;
and wherein the variant has alpha-amylase activity.
3. The variant of Embodiment 1 or 2, which is an isolated alpha-amylase variant.
4. The variant of any of the preceding embodiments, wherein the variant comprises or has the following or corresponding group a) and group b) substitutions:
group a): K176L+E185P+I201Y+H205Y+K213T+Q360S+D416V+R437W; or K176L+I201Y+H205Y+K213T+E255P+Q360S+D416V+R437W and
one or more of the following substitutions in group b):
K136, K154, K170, K234, K237, K251, K306, K315, K319, K392 (using SEQ ID NO: 1 for numbering).
5. The variant of embodiment 4, wherein the group b) substitution is K136R (using SEQ ID NO: 1 for numbering).
6. The variant of embodiment 4, wherein the group b) substitution is K154A, H, S (using SEQ ID NO: 1 for numbering).
7. The variant of embodiment 4, wherein the group b) substitution is K170R, S (using SEQ ID NO: 1 for numbering).
8. The variant of embodiment 4, wherein the group b) substitution is K234T (using SEQ ID NO: 1 for numbering).
9. The variant of embodiment 4, wherein the group b) substitution is K237R (using SEQ ID NO: 1 for numbering).
10. The variant of embodiment 4, wherein the group b) substitution is K306M or K251Q (using SEQ ID NO: 1 for numbering).
11. The variant of embodiment 4, wherein the group b) substitution is K315A, N, C, Q, E, G, H, I, L, M, F, P, S, T, W, Y, V (using SEQ ID NO: 1 for numbering).
12. The variant of embodiment 4, wherein the group b) substitution is K319Q, L (using SEQ ID NO: 1 for numbering).
13. The variant of any of the preceding embodiments, wherein the group b) substitutions are selected from the group consisting of:
K136R;
K154A;
K154H;
K154S;
K170R;
K170S;
K234T;
K237R;
K251Q;
K306M
K315M;
K319Q;
K319L;
K392V;
K392V+Q393D; and
H133Y+K136R (using SEQ ID NO: 1 for numbering).
14. The variant of any of the preceding embodiments, wherein the variant further comprises a substitution in any of positions H68, H133, H142, Y156, Y158, H316, L318; preferably H68W, H133Y, H142Y, Y156W, Y158W, H316W, L318W; using SEQ ID NO: 1 for numbering.
15. The variant of any of the preceding embodiments, wherein the variant has at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of any of SEQ ID NO: 1, or (ii) amino acids 1 to 483 of SEQ ID NO: 1.
16. The variant of any of the preceding embodiments, which is a variant of a parent alpha-amylase, which parent alpha-amylase has at least 80%, at least 85%, at least 90%, at least 95%, at least 96%, at least 97%, at least 98%, at least 99% or 100% sequence identity to (i) the mature polypeptide of any of SEQ ID NO: 1, or (ii) amino acids 1 to 483 of SEQ ID NO: 1.

17. The variant of any of embodiments 1-3, wherein the variant comprises or has the following or corresponding group a) and group b) substitutions:
group a): K174L+E183P+F199Y+H203Y+K211+Q358S+ D414V+R435W; or
K174L+F199Y+H203Y+K211T+E253P+Q358S+D414V+ R435W and
one or more of the following substitutions in group b): K134, K152, K168, K232, K235, K249, K304M, K313, K317, K390 (using SEQ ID NO: 14 for numbering).

18. The variant of embodiment 17, wherein the group b) substitution is K134R (using SEQ ID NO: 14 for numbering).

19. The variant of embodiment 17, wherein the group b) substitution is K152A, H, S (using SEQ ID NO: 14 for numbering).

20. The variant of embodiment 17, wherein the group b) substitution is K168R, S (using SEQ ID NO: 14 for numbering).

21. The variant of embodiment 17, wherein the group b) substitution is K232T (using SEQ ID NO: 14 for numbering).

22. The variant of embodiment 17, wherein the group b) substitution is K235R (using SEQ ID NO: 14 for numbering).

23. The variant of embodiment 17, wherein the group b) substitution is K249Q (using SEQ ID NO: 14 for numbering).

24. The variant of embodiment 17, wherein the group b) substitution is K313A, N, C, Q, E, G, H, I, L, M, F, P, S, T, W, Y, V (using SEQ ID NO: 14 for numbering).

25. The variant of embodiment 17, wherein the group b) substitution is K317Q, L (using SEQ ID NO: 14 for numbering).

26. The variant of embodiment 17, wherein the group b) substitution is K390V (using SEQ ID NO: 14 for numbering).

27. The variant of any of embodiments 17-26, wherein the group b) substitutions are selected from the group consisting of:
K134R;
K152A;
K152H;
K152S;
K168R;
K168S;
K232T;
K235R;
K249Q;
K304M
K313M;
K317Q;
K317L;
K390V;
K390V+Q391 D;
H131Y+K134R (using SEQ ID NO: 14 for numbering).

28. The variant of any of embodiments 17-27, further includes a substitution in any of positions H66, H131, H140, Y154, Y156, H314, L316; preferably one or more of the following substitutions: H66W, H131Y, H140Y, Y154W, Y156W, H314W, L316W; using SEQ ID NO: 14 for numbering.

29. The variant of any of Embodiments 1, 2, and 17-28, wherein the variant has at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 14, or (ii) amino acids 1-481 of SEQ ID NO: 14.

30. The variant of any of Embodiments 1, 2, and 17-28, which is a variant of a parent alpha-amylase, which parent alpha-amylase has at least 85%, at least 90%, at least 95%, at least 96%, at least 97%, at least 98%, at least 99% or 100% sequence identity to (i) the mature polypeptide of any of SEQ ID NO: 14, or (ii) amino acids 1 to 481 of SEQ ID NO: 14.

31. The variant of any of the preceding embodiments, wherein the parent alpha-amylase is a fragment of the mature polypeptide of SEQ ID NOs: 1 or 14, wherein the fragment has alpha-amylase activity.

32. The variant of any of the preceding embodiments, which has improved stability, in particular improved stability in the presence of glucose compared to the mature polypeptide of SEQ ID NO: 1 or 14, respectively.

33. The variant of any of the preceding embodiments, wherein the variant has at least 80%, but less than 100% sequence identity to the mature polypeptide of any of SEQ ID NO: 1 and has improved stability, in particular improved stability in the presence of glucose, compared to the mature polypeptide of SEQ ID NO: 1.

34. The variant of any of the preceding embodiments, wherein the variant has at least 80%, but less than 100% sequence identity to amino acids 1 to 483 of SEQ ID NO: 1 and has improved stability, in particular improved stability in the presence of glucose, compared to amino acids 1 to 483 of SEQ ID NO: 1.

35. The variant of any of the preceding embodiments, wherein the variant has at least 80%, but less than 100% sequence identity to the mature polypeptide of any of SEQ ID NO: 1 and has improved stability, in particular improved stability in the presence of glucose, compared to the mature polypeptide of SEQ ID NO: 14.

36. The variant of any of the preceding embodiments, wherein the variant has at least 80%, but less than 100% sequence identity to amino acids 1 to 483 of SEQ ID NO: 1 and has improved stability, in particular improved stability in the presence of glucose, compared to amino acids 1 to 481 of SEQ ID NO: 14.

37. The variant of any of the preceding embodiments, wherein the stability is determined by calculating the residual activity as the ratio between the alpha-amylase activity present after incubation of said variant with 10% (w/w) glucose for 6 hours at 60° C. to the activity present after incubation of said variant with 10% (w/w) glucose for 6 hours at 4° C.

38. The variant of any of the preceding embodiments, wherein the stability of said variant when determined as the ratio between the alpha-amylase activity present after incubation of said variant with 10% (w/w) glucose for 6 hours at 60° C. to the activity present after incubation of said variant with 10% (w/w) glucose for 6 hours at 4° C. is at least 35%, such as at least 36%, 37%, 38%, 39%, 40%, 41%, 42%, 43%, 44%, 45%, 46%, 47%, 48%, 49%, 50%, 55%, 60%, 65%, 70%, 75% or at least 80%.

39. The variant of any of the preceding embodiments, which has a relatively higher activity on long chain versus short chain substrates as compared to the mature polypeptide of SEQ ID NO: 1 or 14, respectively.

40. An isolated polynucleotide encoding the variant of any of Embodiments 1-39.

41. A nucleic acid construct comprising the polynucleotide of Embodiment 40.
42. An expression vector comprising the polynucleotide of Embodiment 40 or the construct of Embodiment 41.
43. A host cell comprising the polynucleotide of Embodiment 42.
44. A method of producing an alpha-amylase variant, comprising:
a. cultivating the host cell of embodiment 43 under conditions suitable for expression of the variant; and
b. recovering the variant.
45. A method for obtaining an alpha-amylase variant, comprising (a) introducing into a parent alpha-amylase a substitution as defined in any of embodiments 1-39; and (b) recovering the variant.
46. A composition comprising the variant of any of embodiments 1 to 39 and one or more enzymes selected from the group consisting of beta-amylase, cellulase (beta-glucosidase, cellobiohydrolase, and endoglucanase) glucoamylase, hemicellulase (e.g., xylanase), isoamylase, isomerase, lipase, phytase, protease and pullulanase.
47. A process of producing liquefied starch, comprising liquefying a starch-containing material with the variant of any of embodiments 1 to 39 or a composition of embodiment 4634.
48. A process of producing a fermentation product, comprising
(a) liquefying a starch-containing material with the variant of any of embodiments 1 to 39 to produce a liquefied mash;
(b) saccharifying the liquefied mash to produce fermentable sugars; and
(c) fermenting the fermentable sugars in the presence of a fermenting organism.
49. The process of embodiment 48, wherein the temperature during liquefaction in step (a) is above the initial gelatinization temperature, such as between 80-90° C., such as around 85° C.
50. The process of any of embodiments 47-49, wherein step (a) is performed at pH 4-6, preferably 4.2-5.5, such as around 4.5.
51. The process of any of Embodiments 47-50, wherein liquefaction in step (a) is carried out for 0.1-12 hours, such as 0.5-5 hours.
52. The process of any of Embodiments 47-51, wherein the temperature during step (b) or pre-saccharification is in the range from 30-70° C., such as 55-65° C., typically around 60° C.
53. The process of any of Embodiments 47-52, wherein saccharification in step (b), or simultaneous saccharification and fermentation, is done using a carbohydrate-source generating enzyme, such as a glucoamylase.
54. The process of any of Embodiments 47-53, wherein saccharification in step (b) and fermentation in step (c) are done sequentially or simultaneously.
55. The process of any of embodiments 47-54, wherein the temperature during step (c) or simultaneous steps (b) and (c) is from 25° C. to 40° C., such as from 28° C. to 35° C., such as from 30° C. to 34° C., preferably around about 32° C.
56. The process of any of Embodiments 47-55, wherein fermentation is step (c) or simultaneous steps (b) and (c) is done using a yeast, such as *Saccharomyces*, such as especially *Saccharomyces cerevisae*.
57. The process of embodiment 47, wherein the temperature during liquefaction in step (a) is at a temperature below or just above the initial gelatinization temperature of said granular starch, such at least 58° C., such as about 60-70° C.
58. The process of any of embodiments 47-57, wherein the pH is in the range of 3.0 to 7.0, preferably from 3.5 to 6.0, preferably from 4.0-5.0, preferably 4.5-5.5, more preferably 4.5.
59. A process of producing sugars, comprising
(a) liquefying a starch-containing material with an alpha-amylase variant of any of Embodiments 1 to 33 to produce a liquefied mash;
(b) saccharifying the liquefied mash to produce fermentable sugars.
60. The process of embodiment 59, wherein the temperature during step (a) is above the initial gelatinization temperature, such as between 80-90° C., such as around 85° C.
61. The process of Embodiments 59 or 60, wherein step (a) is performed at pH 4-6, such as pH 4.5-5.5, such as pH 4-5.
62. The process of any of Embodiments 59-61, wherein liquefaction in step (a) is carried out for 0.1-12 hours, such as 0.5-5 hours.
63. The process of any of Embodiments 59-62, wherein the temperature during step (b) or pre-saccharification is in the range between 30-70° C., such as 55-65° C., typically around 60° C.
64. The process of any of Embodiments 59-63, wherein saccharification in step (b), or simultaneous saccharification and fermentation, is done using a carbohydrate-source generating enzyme, such as a glucoamylase.
65. The process of any of Embodiments 59-64, wherein sugars are recovered after saccharification step (b).
66. The process of any of Embodiments 59-65, wherein sugars obtained in step (b) are further processes to, e.g., high fructose syrup, e.g., using an immobilized glucose isomerase.
67. The process of embodiment 59, wherein the temperature during liquefaction in step (a) is at a temperature below or just above the initial gelatinization temperature of said granular starch, such at least 58° C., such as about 60-70° C.
68. The process of any of embodiments 59-67, wherein the pH is in the range of 3.0 to 7.0, preferably from 3.5 to 6.0, preferably from 4.0-5.0, preferably 4.5-5.5, more preferably 4.5.
69. Use of the variant of any of Embodiments 1-39 for washing and/or dishwashing.
70. Use of the variant of any of Embodiments 1-39 for desizing a textile.
71. Use of the variant of any of Embodiments 1-39 for producing a baked product.
72. Use of the variant of any of Embodiments 1-39 for liquefying a starch-containing material.
73. Use of the variant of any of Embodiments 1-39 for liquefying a starch-containing material in a process of producing syrups.
74. Use of the variant of any of Embodiments 1-39 for liquefying a starch-containing material in a process of producing a fermentation product, such as ethanol.

ENZYMES

Carbohydrate-Source Generating Enzyme

The term "carbohydrate-source generating enzyme" includes glucoamylase (being glucose generators), beta-amylase and maltogenic amylase (being maltose generators). A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Especially contemplated mixtures are mixtures of at least a glucoamylase and an alpha-amylase, especially an acid amylase, even more preferred an acid fungal alpha-amylase. The ratio between acid fungal alpha-amylase activity (AFAU) per glucoamylase activity (AGU) (AFAU per AGU) may in an embodiment of the invention be at least 0.1, or at least 0.16, such as in the range from 0.12 to 0.50 or more.

The ratio between acid fungal alpha-amylase activity (FAU-F) and glucoamylase activity (AGU) (i.e., FAU-F per AGU) may in an embodiment of the invention be between 0.1 and 100, in particular between 2 and 50, such as in the range from 10-40.

Glucoamylase

A glucoamylase used according to the invention may be derived from any suitable source, e.g., derived from a microorganism or a plant. Preferred glucoamylases are of fungal or bacterial origin, selected from the group consisting of *Aspergillus* glucoamylases, in particular *A. niger* G1 or G2 glucoamylase (Boel et al., 1984, *EMBO J.* 3 (5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (*Agric. Biol. Chem.*, 1991, 55 (4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, Biochem. J. 301: 275-281); disulphide bonds, A246C (Fierobe et al., 1996, *Biochemistry* 35: 8698-8704; and introduction of Pro residues in position A435 and S436 (Li et al., 1997, *Protein Eng.* 10: 1199-1204.

Other glucoamylases include Athelia *rolfsii* (previously denoted *Corticium rolfsii*) glucoamylase (see U.S. Pat. No. 4,727,026 and Nagasaka et al., 1998, "Purification and properties of the raw-starch-degrading glucoamylases from *Corticium rolfsii*, *Appl Microbiol Biotechnol* 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti*, and *Talaromyces thermophilus* (U.S. Pat. No. 4,587,215).

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulata, Pachykytospora papyracea*; and *Leucopaxillus giganteus* all disclosed in WO 2006/069289; and *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus* as described in WO 2011/066576 (SEQ ID NOs 2, 4 or 6), or from a strain of the genus *Gloephyllum*, in particular a strain of *Gloephyllum* as described in WO 2011/068803 (SEQ ID NO: 2, 4, 6, 8, 10, 12, 14 or 16) or a strain of the genus *Nigrofomes*, in particular a strain of *Nigrofomes* sp. disclosed in WO 2012/064351 (SEQ ID NO: 2) (all references hereby incorporated by reference). Contemplated are also glucoamylases which exhibit a high identity to any of the above-mentioned glucoamylases, i.e., at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME ULTRA™ and AMG™ E (from Novozymes A/S, Denmark); OPTIDEX™ 300, GC480™ and GC147™ (from Genencor Int., USA); AMIGASE™ and AMIGASE™ PLUS (from DSM); G-ZYME™ G900, G-ZYME™ and G990 ZR (from Genencor Int.).

Glucoamylases may in an embodiment be added in an amount of 0.02-20 AGU/g DS, preferably 0.1-10 AGU/g DS, especially between 1-5 AGU/g DS, such as 0.1-2 AGU/g DS, such as 0.5 AGU/g DS or in an amount of 0.0001-20 AGU/g DS, preferably 0.001-10 AGU/g DS, especially between 0.01-5 AGU/g DS, such as 0.1-2 AGU/g DS.

Beta-Amylase

At least according to the invention the a beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (W. M. Fogarty and C. T. Kelly, 1979, *Progress in Industrial Microbiology* 15: 112-115). These beta-amylases are characterized by having optimum temperatures in the range from 40° C. to 65° C. and optimum pH in the range from 4.5 to 7. A commercially available beta-amylase from barley is NOVOZYM™ WBA from Novozymes A/S, Denmark and SPEZYME™ BBA 1500 from Genencor Int., USA.

Maltoqenic Amylase

The amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may in a preferred embodiment be added in an amount of 0.05-5 mg total protein/gram DS or 0.05-5 MANU/g DS.

Proteases

A protease used in accordance with the invention be any protease, such as of microbial or plant origin. In a preferred embodiment the protease is an acid protease of microbial origin, preferably of fungal or bacterial origin.

Suitable proteases include microbial proteases, such as fungal and bacterial proteases. Preferred proteases are acidic proteases, i.e., proteases characterized by the ability to hydrolyze proteins under acidic conditions below pH 7.

Contemplated acid fungal proteases include fungal proteases derived from *Aspergillus, Mucor, Rhizopus, Candida, Coriolus, Endothia, Enthomophtra, Irpex, Penicillium, Scle-*

*rotium* and *Torulopsis*. Especially contemplated are proteases derived from *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), *Aspergillus awamori* (Hayashida et al., 1977, *Agric. Biol. Chem.* 42(5): 927-933, *Aspergillus aculeatus* (WO 95/02044), or *Aspergillus oryzae*, such as the pepA protease; and acidic proteases from *Mucor pusillus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No. P06832.

Also contemplated are the proteases having at least 90% identity to amino acid sequence obtainable at Swissprot as Accession No. P06832 such as at least 92%, at least 95%, at least 96%, at least 97%, at least 98%, or particularly at least 99% identity.

Further contemplated are the proteases having at least 90% identity to amino acid sequence disclosed as SEQ. ID. NO: 1 in the WO 2003/048353 such as at 92%, at least 95%, at least 96%, at least 97%, at least 98%, or particularly at least 99% identity.

Also contemplated are papain-like proteases such as proteases within E.C. 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

In an embodiment the protease is a protease preparation derived from a strain of *Aspergillus*, such as *Aspergillus oryzae*. In another embodiment the protease is derived from a strain of *Rhizomucor*, preferably *Rhizomucor miehei*. In another contemplated embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor mehei*.

Aspartic acid proteases are described in, for example, Handbook of Proteolytic Enzymes, Edited by Barrett, Rawlings and Woessner, Academic Press, San Diego, 1998, Chapter 270). Suitable examples of aspartic acid protease include, e.g., those disclosed in Berka et al., 1990, *Gene* 96: 313; Berka et al., 1993, *Gene* 125: 195-198; and Gomi et al., 1993, *Biosci. Biotech. Biochem.* 57: 1095-1100, which are hereby incorporated by reference.

Commercially available products include ALCALASE®, ESPERASE™, FLAVOURZYME™ PROMIX™, NEUTRASE®, RENNILASE®, NOVOZYM™ FM 2.0L, and NOVOZYM™ 50006 (available from Novozymes A/S, Denmark) and GC106™ and SPEZYME™ FAN from Genencor Int., Inc., USA.

The protease may be present in an amount of 0.0001-1 mg enzyme protein per g DS, preferably 0.001 to 0.1 mg enzyme protein per g DS. Alternatively, the protease may be present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS or 0.1-1000 AU/kg DS, preferably 1-100 AU/kg DS and most preferably 5-25 AU/kg DS.

Materials & Methods
Assays for Measurement of Amylolytic Activity (Alpha-Amylase Activity)
PNP-G7 Assay:

The alpha-amylase activity is determined by a method employing the PNP-G7 substrate. PNP-G7 is an abbreviation for 4,6-ethylidene($G_7$)-p-nitrophenyl($G_1$)-α,D-maltoheptaoside, a blocked oligosaccharide which can be cleaved by an endo-amylase, such as an alpha-amylase. Following the cleavage, the alpha-glucosidase included in the kit digest the hydrolysed substrate further to liberate a free PNP molecule which has a yellow color and thus can be measured by visible spectophometry at λ=405 nm (400-420 nm.). Kits containing PNP-G7 substrate and alpha-glucosidase is manufactured by Roche/Hitachi (cat. No. 11876473).

Reagents:

The G7-PNP substrate from this kit contains 22 mM 4,6-ethylidene-G7-PNP and 52.4 mM HEPES (2-[4-(2-hydroxyethyl)-1-piperazinyl]-ethanesulfonic acid), pH 7.0.

The alpha-glucosidase reagent contains 52.4 mM HEPES, 87 mM NaCl, 12.6 mM $MgCl_2$, 0.075 mM $CaCl_2$, >4 kU/L alpha-glucosidase.

The substrate working solution is made by mixing 1 ml of the alpha-glucosidase reagent with 0.2 ml of the G7-PNP substrate. This substrate working solution is made immediately before use.

Dilution buffer: 50 mM EPPS, 0.01% (w/v) Triton X100 (polyethylene glycol p-(1,1,3,3-tetramethylbutyl)-phenyl ether ($C_{14}H_{22}O(C_2H_4O)_n$ (n=9-10))), 1 mM $CaCl_2$, pH 7.0.

Procedure:

The amylase sample to be analyzed is diluted in dilution buffer to ensure the pH in the diluted sample is 7. The assay is performed by transferring 20 µl diluted enzyme samples to 96 well microtiter plate and adding 80 µl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Phadebas Activity Assay:

The alpha-amylase activity can also be determined by a method using the Phadebas substrate (from for example Magle Life Sciences, Lund, Sweden). A Phadebas tablet includes interlinked starch polymers that are in the form of globular microspheres that are insoluble in water. A blue dye is covantly bound to these microspheres. The interlinked starch polymers in the microsphere are degraded at a speed that is proportional to the alpha-amylase activity. When the alpha-amylse degrades the starch polymers, the released blue dye is water soluble and concentration of dye can be determined by measuring absorbance at 620 nm. The concentration of blue is proportional to the alpha-amylase activity in the sample.

The amylase sample to be analysed is diluted in dilution buffer with the desired pH. One substrate tablet is suspended in 5 mL activity buffer and mixed on magnetic stirrer. During mixing of substrate transfer 150 µl to microtiter plate (MTP) or PCR-MTP. Add 30 µl diluted amylase sample to 150 µl substrate and mix. Incubate for 15 minutes at 37° C. The reaction is stopped by adding 30 µl 1M NaOH and mix. Centrifuge MTP for 5 minutes at 4000×g. Transfer 100 µl to new MTP and measure absorbance at 620 nm.

The amylase sample should be diluted so that the absorbance at 620 nm is between 0 and 2.2. A similar protocol can be used with the Amylazym™ substrate from Megazyme, Inc., Ireland.

EnzChek® Assay:

For the determination of residual amylase activity an EnzChek® Ultra Amylase Assay Kit (E33651, Invitrogen, La Jolla, Calif., USA) was used.

The substrate is a corn starch derivative, DQ™ starch, which is corn starch labeled with BODIPY® FL dye to such a degree that fluorescence is quenched. One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.125 mM $CaCl_2$, pH 5.5 is added, vortexed thoroughly and stored at room temperature, in the dark until ready to use. The stock substrate working solution is prepared by diluting 10-fold in residual activity buffer (100 mM acetate, 0.01% (w/v) TRITON® X100, 0.125 mM $CaCl_2$, pH 5.5). Immediately after incubation the enzyme is diluted to a concentration of 10-20 ng enzyme protein/ml in 100 mM acetate, 0.01% (W/v) TRITON® X100, 0.125 mM $CaCl_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.

Glucoamylase Activity (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
| --- | --- |
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
| --- | --- |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Beta-Amylase Activity (BAMU)

Beta-amylase activity in BAMU is measured relative to a Novozymes beta-amylase standard. Beta-amylase acts on the non-reducing end of maltohexaose (G6) to form maltose (G2) and maltotetraose (G4). Produced G4 reacts stronger than G6 in the presence of lactose-oxidase and O2 to form H2O2. The formed H2O2 activates in the presence of peroxidase the oxidative condensation of 4-aminoantipyrine (AA) and N-ethyl-N-sulfopropyl-m-toluidine (TOPS), to form a purple product which can be quantified by its absorbance at 540 nm.

| Reaction conditions | |
| --- | --- |
| Buffer | 67 mM phosphate and 67 mM citrate |
| pH | 5.5 |
| Beta-amylase | 0.083-0.166 BAMU/mL |
| Maltohexaose | 0.856 mM |
| Lactose oxidase | 4.8 LOXU/mL |
| 4-Aminoantipyrine (AA) | 1.7 mM |
| N-ethyl-N-sulfopropyl-m-toluidine (TOPS) | 4.3 mM |
| Peroxidase (Sigma) | 2.1 U/mL |
| Temperature: | 37° C. |
| Reaction time: | 200 seconds |
| Wavelength | 540 nm |

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M Ca2+; and pH 5.6) dextrinizes 5260 mg starch dry substance Merck Amylum solubile.

Determination of FAU Activity

One Fungal Alpha-Amylase Unit (FAU) is defined as the amount of enzyme, which breaks down 5.26 g starch (Merck Amylum solubile Erg. B.6, Batch 9947275) per hour based upon the following standard conditions:

Substrate Soluble starch
Temperature 37° C.
pH 4.7
Reaction time 7-20 minutes

Determination of Acid Alpha-Amylase Activity (AFAU)

Acid alpha-amylase activity is measured in AFAU (Acid Fungal Alpha-amylase Units), which are determined relative to an enzyme standard.

The standard used is AMG 300 L (from Novozymes A/S, glucoamylase wildtype *Aspergillus niger* G1, also disclosed in Boel et al. (1984), *EMBO J.* 3 (5), p. 1097-1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

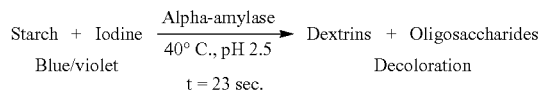

Standard conditions/reaction conditions: (per minute)
Substrate: Starch, approx. 0.17 g/L
Buffer: Citate, approx. 0.03 M
Iodine (I2): 0.03 g/L
CaCl2: 1.85 mM
pH: 2.50±0.05
Incubation temperature: 40° C.
Reaction time: 23 seconds
Wavelength: lambda=590 nm
Enzyme concentration: 0.025 AFAU/mL
Enzyme working range: 0.01-0.04 AFAU/mL Determination of Maltogenic Amylase Activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37° C. for 30 minutes.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 ml diluted sample or standard is incubated at 40° C. for 2 minutes. 0.5 ml 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

Determination of Sugar Profile and Solubilised Dry Solids

The sugar composition of the starch hydrolysates is determined by HPLC and glucose yield is subsequently calculated as DX. ° BRIX, solubilized (soluble) dry solids of the starch hydrolysates are determined by refractive index measurement.

Protease Assay Method—AU(RH)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e., 25° C., pH 5.5 and 10 min. reaction time) digests hemoglobin at an initial rate such that there is liberated per minute an amount of TCA soluble product which gives the same color with phenol reagent as one milliequivalent of tyrosine.

Proteolytic Activity (AU)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU) is defined as the amount of enzyme which under standard conditions (i.e., 25° C., pH 7.5 and 10 min. reaction time) digests hemoglobin at an initial rate such that there is liberated per minute an amount of TCA soluble product which gives the same color with phenol reagent as one milliequivalent of tyrosine.

Protease Assay Method (LAPU)

1 Leucine Amino Peptidase Unit (LAPU) is the amount of enzyme which decomposes 1 microM substrate per minute at the following conditions: 26 mM of L-leucine-p-nitroanilide as substrate, 0.1 M Tris buffer (pH 8.0), 37° C., 10 minute reaction time.

Materials
Alpha-Amylase Variants

The alpha-amylase variants tested are variants of LE399 (SEQ ID NO: 14, previously disclosed in, e.g., WO 2002/010355). LE399 comprises amino acids 1-37 of the alpha-amylase from Bacillus amyloliquefaciens (SEQ ID NO: 6) and amino acids 40-483 of the alpha-amylase from Bacillus licheniformis (SEQ ID NO: 1) with the following substitutions G48A T49I G107A H156Y A181T N190F I201F A209V Q264S. The substitutions in each variant as listed below are substitutions as compared to LE399. The position numbering is according to SEQ ID NO: 1.

LE399 is two amino acids shorter than SEQ ID NO: 1 in the N-terminal, i.e. there are no amino acids corresponding to positions 1 and 2 of SEQ ID NO: 1 in LE399. The alteration denoted in the tables as *2aH means insertion of H before the N-terminal V of LE399. A similar alteration in SEQ ID NO: 1 would be substitution of amino acid N2 with H, i.e. N2H (alternatively, deletion of amino acid A1 combined with substitution of amino acid N2 with H, i.e. A1*N2H). Likewise, the alterations denoted in the tables as *2aH *2bW means insertion of HW before the N-terminal V of LE399. A similar alteration in SEQ ID NO: 1 would be the substitutions A1H N2W.

Alpha-Amylase Variant E:
K176L+E185P+F201Y+H205Y+K213T+K315M+Q360S+ D416V+R437W

Alpha-Amylase Variant F:
K176L+F201Y+H205Y+K213T+E255P+Q360S+D416V+ R437W

Glucoamylase

Glucoamylase A: Glucoamylase from *Trametes cingulata* (WO 2006/069289).

Glucoamylase B: Glucoamylase from *Aspergillus niger* (Glucoamylase G1 derived from *Aspergillus niger* disclosed in Boel et al. (1984), *EMBO J.* 3 (5), 1097-1102, available from Novozymes A/S).

Glucoamylase C: Glucoamylase from *Gloeophyllum trabeum* disclosed in application no.
EP13165995 as variant having the double substitution S95P, A121P.

Beta-Amylase

Beta-Amylase A: Optimalt BBA (available from DuPont).
Beta-Amylase B: Beta-amylase from *Bacillus flexus* (U.S. Pat. No. 8,486,682).

Comparative Alpha-Amylase

Comparative alpha-amylase variants are also variants of LE399 (SEQ ID NO: 14, previously disclosed in, e.g., WO 2002/010355), as described in e.g., WO 2013/057143. LE399 comprises amino acids 1-37 of the alpha-amylase from *Bacillus amyloliquefaciens* (SEQ ID NO: 6) and amino acids 40-483 of the alpha-amylase from *Bacillus licheniformis* (SEQ ID NO: 1) with the following substitutions G48A T49I G107A H156Y A181T N190F I201F A209V Q264S. The substitutions in each variant as listed below are substitutions as compared to LE399. The position numbering is according to SEQ ID NO: 1.

LE399 is two amino acids shorter than SEQ ID NO: 1 in the N-terminal, i.e. there are no amino acids corresponding to positions 1 and 2 of SEQ ID NO: 1 in LE399. The alteration denoted in the tables as *2aH means insertion of H before the N-terminal V of LE399. A similar alteration in SEQ ID NO: 1 would be substitution of amino acid N2 with H, i.e. N2H (alternatively, deletion of amino acid A1 combined with substitution of amino acid N2 with H, i.e. A1*N2H). Likewise, the alterations denoted in the tables as *2aH *2bW means insertion of HW before the N-terminal V of LE399. A similar alteration in SEQ ID NO: 1 would be the substitutions A1H N2W.

Comparative Alpha-Amylase 1:
H68W+K176L+E185P+I201Y+H205Y+K213T+Q360S+D416V+R437W Example 1

A slurry with 30% dry solids (DS) granular starch is prepared by adding common corn starch under stirring to water. The pH is adjusted with HCl to 4.5. The granular starch slurry is distributed to 100 ml blue cap flasks with 75 g in each flask. The flasks are incubated with magnetic stirring in a 60° C. water bath. At zero hours the 0.05 mg/g DS alpha-amylase variant and 0.1 mg/g DS glucoamylase are dosed to the flasks. Samples are withdrawn after 4, 24 and 48 hours, as indicated.

Total dry solids starch is determined using the following method. The starch is completely hydrolyzed by adding an excess amount of alpha-amylase (300 KNU/Kg dry solids) and subsequently placing the sample in an oil bath at 95° C. for 45 minutes. After filtration through a 0.22 microM filter the dry solids is measured by refractive index measurement.

Soluble dry solids in the starch hydrolysate are determined on samples after filtering through a 0.22 microM filter. Soluble dry solids are determined by refractive index measurement and the sugar profile was determined by HPLC. The amount of glucose is calculated as % DX.

Example 2

Powdered corn starch is combined in a plastic flask with tap water to produce a 31.5% solids starch slurry. The slurry is adjusted to a pH of 4.5 using a 0.1M HCl solution. 20 mL aliquots of this slurry are added to 30 mL Nalgene screw top plastic bottles and the weights were recorded. Each of the enzyme-treated bottles is given an alpha amylase dosage of 0.05 mg enzyme protein per gram of starch dry substance (mg EP/g DS), and a glucoamylase dose of 0.1 mg EP/g DS. Two bottles were left un-dosed as controls. Once dosed, the bottles were placed into two rotisserie ovens which were set to 60° C. or 66° C. respectively.

At various time points (T=4, 24, and 48 hours), 2 mL aliquots are removed from each flask and placed into pre-weighed 15 mL conical spin tubes which were then re-weighed. Each sample is deactivated with 18 µL of 1M HCl. After deactivation, the samples are vortexed completely. The supernatant in each tube is filtered through a 0.45 µm filter disc into microcentrifuge tubes for HPLC analysis. These microcentrifuge tubes are then placed in boiling water for 10 minutes to completely deactivate any enzyme activity. HPLC samples are prepared in vials by diluting 50 µL of the filtered sample in each Eppendorf tube with 950 µL of 0.005M H2SO4 to yield a 20:1 dilution factor.

Once the supernatant is removed from each sample, the tubes are filled to the 10 mL mark with tap water. The tubes are then vortexed and centrifuged as above, then decanted. This process is repeated a second time with tap water, followed by a third and final time with an 80% ethanol solution to remove residual solubles from each tube's solids. These tubes are placed into a 55° C. oven for a minimum of 24 hours before being placed in a 105° C. oven for 24 hours to dry completely. Immediately after being taken out of the oven, the tube caps are closed to prevent the tube contents from picking up moisture. The tubes are then weighed on an analytical balance to determine the weight of the contents.

Determination of Solubilisation by FIS Analysis

The fraction of solids solublized is calculated as follows:

$$\% \text{ Solubilisation} = 1 - \frac{\% \text{ Insoluble Solids In Enzyme Treated Tube}@T_x}{\% \text{ Insuluble Solids In Control Tube}@T_x}$$

HPLC Analysis

HPLC system Agilent's 1100/1200 series with Chem station software

Degasser, Quaternary Pump, Auto-Sampler, Column Compartment w/Heater Refractive Index Detector (RI)

Column Bio-Rad HPX-87H Ion Exclusion Column, 300 mm×7.8 mm, part #125-0140 Bio-Rad guard cartridge cation H, part #125-0129, Holder part #125-0131

Method 0.005M H2SO4 mobile phase

Flow rate: 0.6 ml/min

Column temperature: 65° C.

RI detector temperature: 55° C.

The method quantified analytes using calibration standards for DP4+, DP3, DP2, glucose, fructose, acetic acid, lactic acid, glycerol and ethanol (% w/v). A four point calibration including the origin is used for quantification.

For this experiment, organic acids and fructose HPLC results are not compared among treatments.

Example 3

Powdered corn starch was combined in a plastic flask with DI water to produce a 40.5% solids starch slurry. The slurry was adjusted to a pH of 4.5 using a 0.1M HCl solution. 10 mL aliquots of this slurry were added to 30 mL Nalgene screw top plastic bottles and the weights were recorded. Each of the bottles dosed according to their weights with alpha amylase and glucoamylase enzymes according to Table 1. Sufficient water was added to each bottle to reach 30% dry solids. Bottles 1 and 2 were left undosed and were treated as blanks. Once dosed, the bottles were placed into two rotisserie ovens which were set to 60° C. or 66° C. according to Table 5. The blanks were placed in 60° C. to avoid starch gelatinization.

TABLE 1

Dosing table of alpha-amylase (AA) and glucoamylase (AMG).

| Bottles | Alpha-Amylase (AA) | AMG | AA dose | AMG Dose | Temp (° C.) | pH | DS (%) | total dose |
|---|---|---|---|---|---|---|---|---|
| 1, 2 | Blank (30% solids) | | | | 60 | 4.5 | 30 | 0 |
| 3, 4 | Comparative Alpha-Amylase 1 | Glucoamylase C | 0.045 | 0.09 | 66 | 4.5 | 30 | 0.135 |
| 5, 6 | Comparative Alpha-Amylase 1 | Glucoamylase C | 0.05 | 0.1 | 66 | 4.5 | 30 | 0.15 |
| 7, 8 | Alpha-Amylase Variant E | Glucoamylase C | 0.045 | 0.09 | 66 | 4.5 | 30 | 0.135 |
| 9, 10 | Alpha-Amylase Variant E | Glucoamylase C | 0.05 | 0.1 | 66 | 4.5 | 30 | 0.15 |
| 11, 12 | Alpha-Amylase Variant E | Glucoamylase C | 0.1 | 0.2 | 66 | 4.5 | 30 | 0.3 |
| 13, 14 | Alpha-Amylase Variant E | Glucoamylase C | 0.2 | 0.4 | 66 | 4.5 | 30 | 0.6 |
| 15, 16 | Alpha-Amylase Variant E | Glucoamylase C | 0.1 | 0.1 | 66 | 4.5 | 30 | 0.2 |

At 24 and 48 hour time points, 2 mL aliquots were removed from each flask and placed into pre-weighed 15 mL conical spin tubes which were then re-weighed. Each sample was deactivated with 18 μL of 1M HCL. After deactivation, the samples were vortexed and put in centrifuge for 10 minutes at 3500 rpm. The supernatant in each tube was filtered through a 0.45 μm filter disc into small microcentrifuge tubes for HPLC analysis of hydrolyzate. These microcentrifuge tubes were then placed in boiling water for 10 minutes to completely deactivate any enzyme activity. HPLC samples were prepared in vials by diluting 50 μL of the filtered sample in with 950 μL of mobile phase (5 mM $H_2SO_4$) to yield a 20:1 dilution factor. HPLC samples were analyzed according to procedure described in Example 2. Starch solubilization was also determined according to the procedure described in Example 2.

TABLE 2

Soluble dry solids as percentage of total dry substance average of replicates).

| Treatments | | Comparative Alpha-Amylase 1/ Glucoamylase C | | Alpha-Amylase Variant E/ Glucoamylase C | |
|---|---|---|---|---|---|
| AA dose (mg/gDS) | AMG dose (mg/gDS) | 24 hr | 48 hr | 24 hr | 48 hr |
| 0.045 | 0.09 | 73.2% | 78.0% | 78.4% | 82.5% |
| 0.05 | 0.1 | 76.8% | 80.0% | 80.7% | 84.3% |
| 0.1 | 0.2 | n.d. | n.d. | 89.2% | 92.5% |
| 0.2 | 0.4 | n.d. | n.d. | 93.4% | 95.7% |

*n.d. = not determined

TABLE 3

DX of the soluble hydrolyzate (average of replicates).

| Treatments | | Comparative Alpha-Amylase 1/ Glucoamylase C | | Alpha-Amylase Variant E/ Glucoamylase C | |
|---|---|---|---|---|---|
| AA dose (mg/gDS) | AMG dose (mg/gDS) | 24 hr | 48 hr | 24 hr | 48 hr |
| 0.045 | 0.09 | 97.4% | 96.5% | 97.2% | 96.3% |
| 0.05 | 0.1 | 97.2% | 96.2% | 97.2% | 96.1% |
| 0.1 | 0.2 | n.d. | n.d. | 96.1% | 94.1% |
| 0.2 | 0.4 | n.d. | n.d. | 94.1% | 90.9% |

*n.d. = not determined

This example demonstrates that the tested alpha-amylase variants in combination with glucoamylase effectively solubilize starch (more than 70% in 48 hours) and give a rather high % DX (>95%).

Example 4

Powdered corn starch was combined in a plastic flask with DI water to produce a 40.5% solids starch slurry. The slurry was adjusted to a pH of 4.5 using a 0.1M HCl solution. 10 mL aliquots of this slurry were added to 30 mL Nalgene screw top plastic bottles and the weights were recorded. Each of the bottles dosed according to their weights with alpha amylase and beta amylase enzymes according to Table 4. Sufficient water was added to each bottle to reach 30% dry solids. Bottles 21 and 22 were left undosed and were treated as blanks. Once dosed, the bottles were placed into two rotisserie ovens which were set to 60° C. or 66° C. according to Table 4. The blanks were placed in 60° C. to avoid starch gelatinization.

TABLE 4

Dosing table of alpha-amylase and beta-amylase.

| Bottles | Alpha-Amylase (AA) | Beta-Amylase (BA) | AA dose (mg/gDS) | BA Dose (mg/gDS) | Temp (° C.) | pH | DS (%) | total dose |
|---|---|---|---|---|---|---|---|---|
| 1, 2 | Comparative Alpha-Amylase 1 | Beta-Amylase B | 0.05 | 0.1 | 66 | 4.5 | 30 | 0.15 |
| 3, 4 | Comparative Alpha-Amylase 1 | Beta-Amylase B | 0.05 | 0.15 | 66 | 4.5 | 30 | 0.2 |
| 5, 6 | Alpha-Amylase Variant E | Beta-Amylase A | 0.05 | 0.15 | 66 | 4.5 | 30 | 0.2 |
| 7, 8 | Comparative Alpha-Amylase 1 | Beta-Amylase A | 0.05 | 0.1 | 66 | 4.5 | 30 | 0.15 |
| 9, 10 | Comparative Alpha-Amylase 1 | Beta-Amylase A | 0.05 | 0.15 | 66 | 4.5 | 30 | 0.2 |
| 11, 12 | Alpha-Amylase Variant E | Beta-Amylase A | 0.05 | 0.15 | 66 | 4.5 | 30 | 0.2 |
| 13, 14 | Comparative Alpha-Amylase 1 | Beta-Amylase B | 0.05 | 0.15 | 60 | 4.5 | 30 | 0.2 |
| 15, 16 | Comparative Alpha-Amylase 1 | Beta-Amylase A | 0.05 | 0.15 | 60 | 4.5 | 30 | 0.2 |
| 17, 18 | Alpha-Amylase Variant E | Beta-Amylase B | 0.05 | 0.15 | 60 | 4.5 | 30 | 0.2 |
| 19, 20 | Alpha-Amylase Variant E | Beta-Amylase A | 0.05 | 0.15 | 60 | 4.5 | 30 | 0.2 |
| 21, 22 | Blank (30% solids) | | 0.1 | 0.1 | 60 | 4.5 | 30 | 0.2 |

At 24 and 48 hour time points, 2 mL aliquots were removed from each flask and placed into pre-weighed 15 mL conical spin tubes which were then re-weighed. Each sample was deactivated with 18 µL of 1M HCL. After deactivation, the samples were vortexed and put in centrifuge for 10 minutes at 3500 rpm. The supernatant in each tube was filtered through a 0.45 µm filter disc into small microcentrifuge tubes for HPLC analysis of hydrolyzate. These microcentrifuge tubes were then placed in boiling water for 10 minutes to completely deactivate any enzyme activity. HPLC samples were prepared in vials by diluting 50 µL of the filtered sample in with 950 µL of mobile phase (5 mM $H_2SO_4$) to yield a 20:1 dilution factor. HPLC samples were analyzed according to procedure described in Example 2. Starch solubilization was also determined according to the procedure described in Example 2.

TABLE 5

Soluble dry solids as percentage of total dry substance (average of replicates).

| Treatments | | | Comparative Alpha-Amylase 1 | | | | Alpha-Amylase Variant E | | | |
|---|---|---|---|---|---|---|---|---|---|---|
| | | | Beta-Amylase A | | Beta-Amylase B | | Beta-Amylase A | | Beta-Amylase B | |
| AA dose (mg/gDS) | BA dose (mg/gDS) | Temperature (° C.) | 24 hr | 48 hr | 24 hr | 48 hr | 24 hr | 48 hr | 24 hr | 48 hr |
| 0.05 | 0.1 | 66° C. | 44.7% | 53.0% | 61.7% | 65.5% | n.d. | n.d. | n.d. | n.d. |
| 0.05 | 0.15 | | 46.3% | 53.8% | 59.9% | 66.2% | 52.1% | 59.2% | 65.7% | 71.4% |
| 0.05 | 0.15 | 60° C. | 32.4% | 38.7% | 51.3% | 58.0% | 35.2% | 42.7% | 55.9% | 62.4% |

TABLE 6

% DP2 of soluble hydrolyzate (average of replicates).

| Treatments | | | Comparative Alpha-Amylase 1 | | | | Alpha-Amylase Variant E | | | |
|---|---|---|---|---|---|---|---|---|---|---|
| | | | Beta-Amylase A | | Beta-Amylase B | | Beta-Amylase A | | Beta-Amylase B | |
| AA dose (mg/gDS) | BA dose (mg/gDS) | Temperature (° C.) | 24 hr | 48 hr | 24 hr | 48 hr | 24 hr | 48 hr | 24 hr | 48 hr |
| 0.05 | 0.1 | 66° C. | 19.1% | 20.6% | 42.6% | 40.6% | n.d. | n.d. | n.d. | n.d. |
| 0.05 | 0.15 | | 20.1% | 21.4% | 44.3% | 40.9% | 19.8% | 21.1% | 44.1% | 42.0% |
| 0.05 | 0.15 | 60° C. | 22.3% | 22.9% | 57.0% | 56.2% | 21.7% | 22.1% | 56.3% | 55.5% |

This example demonstrates that the tested alpha-amylase variants in combination with beta-amylase effectively solubilize starch and can work effectively even at higher temperature of 66° C.

Example 5

Two amino acid substitutions, W68H and K315M, were introduced in alpha-amylase variant F (SEQ ID NO: 15) by standard site directed methods. In the resulting alpha-amylase variant, native Lysines were substituted with non-native amino acid residues as indicated in table 7 below. The position numbering is according to SEQ ID NO: 1. The amylase genes were transformed into and expressed in *Bacillus subtilis*. The *bacillus subtilis* broths were centrifuged and the amylase containing supernatants isolated and diluted 50 times in 50 mM NaAcetate buffer pH 4.5 before they was mixed with a glucose solution to a final concentration of 10% glucose. The samples were then split in two, and while one half was stored at 4° C. the other half was incubated at 60° C. for 6 hours. Following that, the samples were diluted 50 times in 100 mM Britton-Robinson buffer (100 mM acetic acid+100 mM phosphate acid+100 mM boric acid, pH 7.3+0.12 mM CaCl2+0.01% Brij, pH adjusted to pH 7.3 and the amylase activity measured using Phadebas amylase assay as described under methods. The residual activities were calculated as the ratio between the activity in the sampled that have been incubated at 60° C. relative to activity in the samples that have been incubated at 4° C.

TABLE 7

Residual activity of alpha-amylase variants after incubation in glucose.

| Amylase | Residual activity after incubation in 10% glucose for 6 hours |
|---|---|
| SEQ ID NO: 15 (LE2488) | 37% |
| SEQ ID NO: 15 + W68H + K315M (reference) | 38% |
| Reference + K170R | 45% |
| Reference + K136Q | 58% |
| Reference + K234T | 42% |
| Reference + K154S | 68% |
| Reference + K251Q | 51% |
| Reference + K392Q | 52% |
| Reference + K154A | 39% |
| Reference + K306M | 79% |
| Reference + K251S | 39% |
| Reference + K136R | 60% |
| Reference + K237A | 48% |
| Reference + K392R + Q393D | 45% |
| Reference + K392V | 61% |

This example demonstrates that alpha-amylase variant having increased stability in the presence of glucose can be generated by substituting Lysine residues with non-native amino acid residues.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. An alpha-amylase variant of a parent alpha-amylase comprising a first substitution 201Y and one or more second substitutions of a lysine residue at one or more positions selected from the group consisting of 237, and 392; wherein
   (a) the variant has at least 95% and less than 100% sequence identity to SEQ ID NO: 14:
   (b) the one or more second substitutions are 237R, and 392V;
   (c) each position corresponds to SEQ ID NO: 1; and
   (d) the variant has alpha-amylase activity.

2. The alpha-amylase variant of claim 1, which further comprises 154S.

3. The alpha-amylase variant of claim 1, which comprises 201Y and 237R.

4. The alpha-amylase variant of claim 1, which further comprises 315M.

5. The alpha-amylase variant of claim 1, which comprises 201Y and 392V.

6. The alpha-amylase variant of claim 1, further comprising one or more third substitutions at one or more positions selected from the group consisting of 68, 133, 136, 142, 154 156, 158, 170, 176, 185, 205, 213, 234, 251, 315, 316, 318, 319, 360, 416 and 437.

7. The alpha-amylase variant of claim 6, wherein the one or more third substitutions are 68W, 133Y, 136R, 142Y, 154S, 156W, 158W, 170R,S, 176L, 185P, 205Y, 213T, 234T, 251Q, 315W, 316W, 318W, 319Q,L, 360S, 416V, and 437W.

8. A detergent composition comprising an alpha-amylase variant of claim 1 and a surfactant.

9. An isolated polynucleotide encoding the alpha-amylase variant of claim 1.

10. A nucleic acid construct or expression vector comprising the polynucleotide of claim 9.

11. A host cell comprising the polynucleotide of claim 9.

12. A method of producing an alpha-amylase variant, comprising:
   (a) cultivating the host cell of claim 11 under conditions suitable for expression of the alpha-amylase variant; and
   (b) recovering the alpha-amylase variant.

13. A process of producing a liquefied mash, comprising liquefying a starch-containing material with the alpha-amylase variant of claim 1 to produce a liquefied mash.

14. A process of producing fermentable sugars, comprising
   (a) liquefying a starch-containing material with the alpha-amylase variant of claim 1 to produce a liquefied mash; and
   (b) saccharifying the liquefied mash to produce fermentable sugars.

15. A process of producing a fermentation product, comprising
   (a) liquefying a starch-containing material with the alpha-amylase variant of claim 1 to produce a liquefied mash;
   (b) saccharifying the liquefied mash to produce fermentable sugars; and
   (c) fermenting the fermentable sugars in the presence of a fermenting organism.

\* \* \* \* \*

SEQUENCE LISTING

<160> NUMBER OF SEQ ID NOS: 15

<210> SEQ ID NO 1
<211> LENGTH: 483
<212> TYPE: PRT
<213> ORGANISM: Bacillus licheniformis

<400> SEQUENCE: 1

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu

```
                20                  25                  30
Ala Glu His Gly Ile Thr Ala Val Trp Ile Pro Pro Ala Tyr Lys Gly
            35                  40                  45
Thr Ser Gln Ala Asp Val Gly Tyr Gly Ala Tyr Asp Leu Tyr Asp Leu
        50                  55                  60
Gly Glu Phe His Gln Lys Gly Thr Val Arg Thr Lys Tyr Gly Thr Lys
65                  70                  75                  80
Gly Glu Leu Gln Ser Ala Ile Lys Ser Leu His Ser Arg Asp Ile Asn
                85                  90                  95
Val Tyr Gly Asp Val Val Ile Asn His Lys Gly Gly Ala Asp Ala Thr
            100                 105                 110
Glu Asp Val Thr Ala Val Glu Val Asp Pro Ala Asp Arg Asn Arg Val
        115                 120                 125
Ile Ser Gly Glu His Leu Ile Lys Ala Trp Thr His Phe His Phe Pro
        130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Asn Glu Asn Gly Asn
            180                 185                 190
Tyr Asp Tyr Leu Met Tyr Ala Asp Ile Asp Tyr Asp His Pro Asp Val
        195                 200                 205
Ala Ala Glu Ile Lys Arg Trp Gly Thr Trp Tyr Ala Asn Glu Leu Gln
        210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
            260                 265                 270
Tyr Leu Asn Lys Thr Asn Phe Asn His Ser Val Phe Asp Val Pro Leu
        275                 280                 285
His Tyr Gln Phe His Ala Ala Ser Thr Gln Gly Gly Gly Tyr Asp Met
        290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Asp Ser Gln Arg Glu Ile Pro Ala Leu Lys His Lys Ile
        370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
            420                 425                 430
Gly Gly Ala Lys Arg Met Tyr Val Gly Arg Gln Asn Ala Gly Glu Thr
        435                 440                 445
```

```
Trp His Asp Ile Thr Gly Asn Arg Ser Glu Pro Val Val Ile Asn Ser
450                 455                 460
Glu Gly Trp Gly Glu Phe His Val Asn Gly Gly Ser Val Ser Ile Tyr
465                 470                 475                 480
Val Gln Arg

<210> SEQ ID NO 2
<211> LENGTH: 515
<212> TYPE: PRT
<213> ORGANISM: Bacillus stearothermophilus

<400> SEQUENCE: 2

Ala Ala Pro Phe Asn Gly Thr Met Met Gln Tyr Phe Glu Trp Tyr Leu
1               5                   10                  15
Pro Asp Asp Gly Thr Leu Trp Thr Lys Val Ala Asn Glu Ala Asn Asn
            20                  25                  30
Leu Ser Ser Leu Gly Ile Thr Ala Leu Trp Leu Pro Pro Ala Tyr Lys
        35                  40                  45
Gly Thr Ser Arg Ser Asp Val Gly Tyr Gly Val Tyr Asp Leu Tyr Asp
    50                  55                  60
Leu Gly Glu Phe Asn Gln Lys Gly Thr Val Arg Thr Lys Tyr Gly Thr
65                  70                  75                  80
Lys Ala Gln Tyr Leu Gln Ala Ile Gln Ala Ala His Ala Ala Gly Met
                85                  90                  95
Gln Val Tyr Ala Asp Val Val Phe Asp His Lys Gly Gly Ala Asp Gly
            100                 105                 110
Thr Glu Trp Val Asp Ala Val Glu Val Asn Pro Ser Asp Arg Asn Gln
        115                 120                 125
Glu Ile Ser Gly Thr Tyr Gln Ile Gln Ala Trp Thr Lys Phe Asp Phe
    130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Ile Gly Lys Ala Trp Asp Trp Glu Val Asp Thr Glu
            180                 185                 190
Asn Gly Asn Tyr Asp Tyr Leu Met Tyr Ala Asp Leu Asp Met Asp His
        195                 200                 205
Pro Glu Val Val Thr Glu Leu Lys Asn Trp Gly Lys Trp Tyr Val Asn
    210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                245                 250                 255
Lys Pro Leu Phe Thr Val Gly Glu Tyr Trp Ser Tyr Asp Ile Asn Lys
            260                 265                 270
Leu His Asn Tyr Ile Thr Lys Thr Asn Gly Thr Met Ser Leu Phe Asp
        275                 280                 285
Ala Pro Leu His Asn Lys Phe Tyr Thr Ala Ser Lys Ser Gly Gly Ala
    290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
```

```
Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
            405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
            450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
            485                 490                 495

Arg Pro Trp Thr Gly Glu Phe Val Arg Trp Thr Glu Pro Arg Leu Val
            500                 505                 510

Ala Trp Pro
515

<210> SEQ ID NO 3
<211> LENGTH: 584
<212> TYPE: PRT
<213> ORGANISM: Bacillus

<400> SEQUENCE: 3

Ala Asn Thr Ala Pro Ile Asn Glu Thr Met Met Gln Tyr Phe Glu Trp
1               5                   10                  15

Asp Leu Pro Asn Asp Gly Thr Leu Trp Thr Lys Val Lys Asn Glu Ala
            20                  25                  30

Ala Asn Leu Ser Ser Leu Gly Ile Thr Ala Leu Trp Leu Pro Pro Ala
            35                  40                  45

Tyr Lys Gly Thr Ser Gln Ser Asp Val Gly Tyr Gly Val Tyr Asp Leu
            50                  55                  60

Tyr Asp Leu Gly Glu Phe Asn Gln Lys Gly Thr Ile Arg Thr Lys Tyr
65                  70                  75                  80

Gly Thr Lys Thr Gln Tyr Ile Gln Ala Ile Gln Ala Ala Lys Ala Ala
            85                  90                  95

Gly Met Gln Val Tyr Ala Asp Val Val Phe Asn His Lys Ala Gly Ala
            100                 105                 110

Asp Gly Thr Glu Phe Val Asp Ala Val Glu Val Asp Pro Ser Asn Arg
            115                 120                 125

Asn Gln Glu Thr Ser Gly Thr Tyr Gln Ile Gln Ala Trp Thr Lys Phe
            130                 135                 140

Asp Phe Pro Gly Arg Gly Asn Thr Tyr Ser Ser Phe Lys Trp Arg Trp
145                 150                 155                 160

Tyr His Phe Asp Gly Thr Asp Trp Asp Glu Ser Arg Lys Leu Asn Arg
            165                 170                 175

Ile Tyr Lys Phe Arg Ser Thr Gly Lys Ala Trp Asp Trp Glu Val Asp
```

```
            180                 185                 190
Thr Glu Asn Gly Asn Tyr Asp Tyr Leu Met Phe Ala Asp Leu Asp Met
            195                 200                 205
Asp His Pro Glu Val Val Thr Glu Leu Lys Asn Trp Gly Thr Trp Tyr
            210                 215                 220
Val Asn Thr Thr Asn Ile Asp Gly Phe Arg Leu Asp Ala Val Lys His
225                 230                 235                 240
Ile Lys Tyr Ser Phe Phe Pro Asp Trp Leu Thr Tyr Val Arg Asn Gln
            245                 250                 255
Thr Gly Lys Asn Leu Phe Ala Val Gly Glu Phe Trp Ser Tyr Asp Val
            260                 265                 270
Asn Lys Leu His Asn Tyr Ile Thr Lys Thr Asn Gly Ser Met Ser Leu
            275                 280                 285
Phe Asp Ala Pro Leu His Asn Asn Phe Tyr Thr Ala Ser Lys Ser Ser
            290                 295                 300
Gly Tyr Phe Asp Met Arg Tyr Leu Leu Asn Asn Thr Leu Met Lys Asp
305                 310                 315                 320
Gln Pro Ser Leu Ala Val Thr Leu Val Asp Asn His Asp Thr Gln Pro
            325                 330                 335
Gly Gln Ser Leu Gln Ser Trp Val Glu Pro Trp Phe Lys Pro Leu Ala
            340                 345                 350
Tyr Ala Phe Ile Leu Thr Arg Gln Glu Gly Tyr Pro Cys Val Phe Tyr
            355                 360                 365
Gly Asp Tyr Tyr Gly Ile Pro Lys Tyr Asn Ile Pro Gly Leu Lys Ser
            370                 375                 380
Lys Ile Asp Pro Leu Leu Ile Ala Arg Arg Asp Tyr Ala Tyr Gly Thr
385                 390                 395                 400
Gln Arg Asp Tyr Ile Asp His Gln Asp Ile Ile Gly Trp Thr Arg Glu
            405                 410                 415
Gly Ile Asp Thr Lys Pro Asn Ser Gly Leu Ala Ala Leu Ile Thr Asp
            420                 425                 430
Gly Pro Gly Gly Ser Lys Trp Met Tyr Val Gly Lys Lys His Ala Gly
            435                 440                 445
Lys Val Phe Tyr Asp Leu Thr Gly Asn Arg Ser Asp Thr Val Thr Ile
            450                 455                 460
Asn Ala Asp Gly Trp Gly Glu Phe Lys Val Asn Gly Gly Ser Val Ser
465                 470                 475                 480
Ile Trp Val Ala Lys Thr Ser Asn Val Thr Phe Thr Val Asn Asn Ala
            485                 490                 495
Thr Thr Thr Ser Gly Gln Asn Val Tyr Val Val Ala Asn Ile Pro Glu
            500                 505                 510
Leu Gly Asn Trp Asn Thr Ala Asn Ala Ile Lys Met Asn Pro Ser Ser
            515                 520                 525
Tyr Pro Thr Trp Lys Ala Thr Ile Ala Leu Pro Gln Gly Lys Ala Ile
            530                 535                 540
Glu Phe Lys Phe Ile Lys Lys Asp Gln Ala Gly Asn Val Ile Trp Glu
545                 550                 555                 560
Ser Thr Ser Asn Arg Thr Tyr Thr Val Pro Phe Ser Ser Thr Gly Ser
            565                 570                 575
Tyr Thr Ala Ser Trp Asn Val Pro
            580

<210> SEQ ID NO 4
```

```
<211> LENGTH: 584
<212> TYPE: PRT
<213> ORGANISM: Bacillus flavothermus

<400> SEQUENCE: 4

Val Pro Val Asn Gly Thr Met Met Gln Tyr Phe Glu Trp Tyr Leu Pro
1               5                   10                  15

Asp Asp Gly Thr Leu Trp Thr Lys Val Ala Asn Asn Ala Gln Ser Leu
            20                  25                  30

Ala Asn Leu Gly Ile Thr Ala Leu Trp Leu Pro Pro Ala Tyr Lys Gly
        35                  40                  45

Thr Ser Ser Ser Asp Val Gly Tyr Gly Val Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Thr Gln Tyr Ile Gln Ala Ile Gln Ala Ala His Thr Ala Gly Met Gln
                85                  90                  95

Val Tyr Ala Asp Val Val Phe Asn His Lys Ala Gly Ala Asp Gly Thr
            100                 105                 110

Glu Leu Val Asp Ala Val Glu Val Asn Pro Ser Asp Arg Asn Gln Glu
        115                 120                 125

Ile Ser Gly Thr Tyr Gln Ile Gln Ala Trp Thr Lys Phe Asp Phe Pro
    130                 135                 140

Gly Arg Gly Asn Thr Tyr Ser Ser Phe Lys Trp Arg Trp Tyr His Phe
145                 150                 155                 160

Asp Gly Thr Asp Trp Asp Glu Ser Arg Lys Leu Asn Arg Ile Tyr Lys
                165                 170                 175

Phe Arg Gly Thr Gly Lys Ala Trp Asp Trp Glu Val Asp Thr Glu Asn
            180                 185                 190

Gly Asn Tyr Asp Tyr Leu Met Tyr Ala Asp Leu Asp Met Asp His Pro
        195                 200                 205

Glu Val Val Ser Glu Leu Lys Asn Trp Gly Lys Trp Tyr Val Thr Thr
    210                 215                 220

Thr Asn Ile Asp Gly Phe Arg Leu Asp Ala Val Lys His Ile Lys Tyr
225                 230                 235                 240

Ser Phe Phe Pro Asp Trp Leu Ser Tyr Val Arg Thr Gln Thr Gln Lys
                245                 250                 255

Pro Leu Phe Ala Val Gly Glu Phe Trp Ser Tyr Asp Ile Ser Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Ile Ala Ser Lys Ser Gly Gly Tyr Phe
    290                 295                 300

Asp Met Arg Thr Leu Leu Asn Asn Thr Leu Met Lys Asp Gln Pro Thr
305                 310                 315                 320

Leu Ala Val Thr Leu Val Asp Asn His Asp Thr Glu Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Ala Leu Lys Ser Lys Leu Asp
    370                 375                 380

Pro Leu Leu Ile Ala Arg Arg Asp Tyr Ala Tyr Gly Thr Gln His Asp
```

-continued

```
                385                 390                 395                 400

Tyr Ile Asp Ser Ala Asp Ile Ile Gly Trp Thr Arg Glu Gly Val Ala
                    405                 410                 415

Glu Lys Ala Asn Ser Gly Leu Ala Ala Leu Ile Thr Asp Gly Pro Gly
                420                 425                 430

Gly Ser Lys Trp Met Tyr Val Gly Lys Gln His Ala Gly Lys Thr Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Pro Lys Ile Ser Thr Thr Ser Gln Ile Thr Phe Thr Val Asn Asn Ala
                485                 490                 495

Thr Thr Val Trp Gly Gln Asn Val Tyr Val Val Gly Asn Ile Ser Gln
                500                 505                 510

Leu Gly Asn Trp Asp Pro Val His Ala Val Gln Met Thr Pro Ser Ser
            515                 520                 525

Tyr Pro Thr Trp Thr Val Thr Ile Pro Leu Leu Gln Gly Gln Asn Ile
        530                 535                 540

Gln Phe Lys Phe Ile Lys Lys Asp Ser Ala Gly Asn Val Ile Trp Glu
545                 550                 555                 560

Asp Ile Ser Asn Arg Thr Tyr Thr Val Pro Thr Ala Ala Ser Gly Ala
                565                 570                 575

Tyr Thr Ala Ser Trp Asn Val Pro
            580

<210> SEQ ID NO 5
<211> LENGTH: 586
<212> TYPE: PRT
<213> ORGANISM: Bacillus

<400> SEQUENCE: 5

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
                20                  25                  30

Ser Leu Ala Asn Leu Gly Ile Thr Ala Leu Trp Leu Pro Pro Ala Tyr
            35                  40                  45

Lys Gly Thr Ser Ser Ser Asp Val Gly Tyr Gly Val Tyr Asp Leu Tyr
        50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
                100                 105                 110

Gly Thr Glu Leu Val Asp Ala Val Glu Val Asn Pro Ser Asp Arg Asn
            115                 120                 125

Gln Glu Ile Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175
```

-continued

```
Tyr Lys Phe Arg Gly Thr Gly Lys Ala Trp Asp Trp Glu Val Asp Thr
                180                 185                 190
Glu Asn Gly Asn Tyr Asp Tyr Leu Met Tyr Ala Asp Leu Asp Met Asp
            195                 200                 205
His Pro Glu Val Val Ser Glu Leu Lys Asn Trp Gly Lys Trp Tyr Val
210                 215                 220
Ile Thr Thr Asn Ile Asp Gly Phe Arg Leu Asp Ala Val Lys His Ile
225                 230                 235                 240
Lys Tyr Ser Phe Phe Pro Asp Trp Leu Ser Tyr Leu Arg Thr Gln Thr
                245                 250                 255
Gln Lys Pro Leu Phe Ala Val Gly Glu Phe Trp Ser Tyr Asp Ile Asn
            260                 265                 270
Lys Leu His Asn Tyr Ile Thr Lys Thr Asn Gly Ser Met Ser Leu Phe
        275                 280                 285
Asp Ala Pro Leu His Asn Asn Phe Tyr Ile Ala Ser Lys Ser Gly Gly
    290                 295                 300
Tyr Phe Asp Met Arg Thr Leu Leu Asn Asn Thr Leu Met Lys Glu Gln
305                 310                 315                 320
Pro Thr Leu Ser Val Thr Leu Val Asp Asn His Asp Thr Glu Pro Gly
                325                 330                 335
Gln Ser Leu Gln Ser Trp Val Glu Pro Trp Phe Lys Pro Leu Ala Tyr
            340                 345                 350
Ala Phe Ile Leu Thr Arg Gln Glu Gly Tyr Pro Cys Val Phe Tyr Gly
        355                 360                 365
Asp Tyr Tyr Gly Ile Pro Lys Tyr Asn Ile Pro Ala Leu Lys Ser Lys
    370                 375                 380
Leu Asp Pro Leu Leu Ile Ala Arg Arg Asp Tyr Ala Tyr Gly Thr Gln
385                 390                 395                 400
His Asp Tyr Ile Asp Asn Ala Asp Ile Ile Gly Trp Thr Arg Glu Gly
                405                 410                 415
Val Ala Glu Lys Ala Asn Ser Gly Leu Ala Ala Leu Ile Thr Asp Gly
            420                 425                 430
Pro Gly Gly Ser Lys Trp Met Tyr Val Gly Lys Gln His Ala Gly Lys
        435                 440                 445
Thr Phe Tyr Asp Leu Thr Gly Asn Arg Ser Asp Thr Val Thr Ile Asn
    450                 455                 460
Ala Asp Gly Trp Gly Glu Phe Lys Val Asn Gly Gly Ser Val Ser Ile
465                 470                 475                 480
Trp Val Pro Lys Thr Ser Thr Ser Gln Ile Thr Phe Thr Val Asn
                485                 490                 495
Asn Ala Thr Thr Val Trp Gly Gln Asn Val Tyr Val Val Gly Asn Ile
            500                 505                 510
Ser Gln Leu Gly Asn Trp Asp Pro Val Asn Ala Val Gln Met Thr Pro
        515                 520                 525
Ser Ser Tyr Pro Thr Trp Val Val Thr Val Pro Leu Pro Gln Ser Gln
    530                 535                 540
Asn Ile Gln Phe Lys Phe Ile Lys Lys Asp Gly Ser Gly Asn Val Ile
545                 550                 555                 560
Trp Glu Asn Ile Ser Asn Arg Thr Tyr Thr Val Pro Thr Ala Ala Ser
                565                 570                 575
Gly Ala Tyr Thr Ala Asn Trp Asn Val Pro
            580                 585
```

```
<210> SEQ ID NO 6
<211> LENGTH: 483
<212> TYPE: PRT
<213> ORGANISM: Bacillus amyloliquefaciens

<400> SEQUENCE: 6
```

| Val | Asn | Gly | Thr | Leu | Met | Gln | Tyr | Phe | Glu | Trp | Tyr | Thr | Pro | Asn | Asp |
|---|---|---|---|---|---|---|---|---|---|---|---|---|---|---|---|
| 1 | | | | 5 | | | | | 10 | | | | | 15 | |

| Gly | Gln | His | Trp | Lys | Arg | Leu | Gln | Asn | Asp | Ala | Glu | His | Leu | Ser | Asp |
| | | | 20 | | | | | 25 | | | | | 30 | | |

| Ile | Gly | Ile | Thr | Ala | Val | Trp | Ile | Pro | Pro | Ala | Tyr | Lys | Gly | Leu | Ser |
| | | | 35 | | | | | 40 | | | | | 45 | | |

| Gln | Ser | Asp | Asn | Gly | Tyr | Gly | Pro | Tyr | Asp | Leu | Tyr | Asp | Leu | Gly | Glu |
| | 50 | | | | | 55 | | | | | 60 | | | | |

| Phe | Gln | Gln | Lys | Gly | Thr | Val | Arg | Thr | Lys | Tyr | Gly | Thr | Lys | Ser | Glu |
| 65 | | | | | 70 | | | | | 75 | | | | | 80 |

| Leu | Gln | Asp | Ala | Ile | Gly | Ser | Leu | His | Ser | Arg | Asn | Val | Gln | Val | Tyr |
| | | | | 85 | | | | | 90 | | | | | 95 | |

| Gly | Asp | Val | Val | Leu | Asn | His | Lys | Ala | Gly | Ala | Asp | Ala | Thr | Glu | Asp |
| | | | 100 | | | | | 105 | | | | | 110 | | |

| Val | Thr | Ala | Val | Glu | Val | Asn | Pro | Ala | Asn | Arg | Asn | Gln | Glu | Thr | Ser |
| | | | 115 | | | | | 120 | | | | | 125 | | |

| Glu | Glu | Tyr | Gln | Ile | Lys | Ala | Trp | Thr | Asp | Phe | Arg | Phe | Pro | Gly | Arg |
| | 130 | | | | | 135 | | | | | 140 | | | | |

| Gly | Asn | Thr | Tyr | Ser | Asp | Phe | Lys | Trp | His | Trp | Tyr | His | Phe | Asp | Gly |
| 145 | | | | | 150 | | | | | 155 | | | | | 160 |

| Ala | Asp | Trp | Asp | Glu | Ser | Arg | Lys | Ile | Ser | Arg | Ile | Phe | Lys | Phe | Arg |
| | | | | 165 | | | | | 170 | | | | | 175 | |

| Gly | Glu | Gly | Lys | Ala | Trp | Asp | Trp | Glu | Val | Ser | Ser | Glu | Asn | Gly | Asn |
| | | | 180 | | | | | 185 | | | | | 190 | | |

| Tyr | Asp | Tyr | Leu | Met | Tyr | Ala | Asp | Val | Asp | Tyr | Asp | His | Pro | Asp | Val |
| | | | 195 | | | | | 200 | | | | | 205 | | |

| Val | Ala | Glu | Thr | Lys | Lys | Trp | Gly | Ile | Trp | Tyr | Ala | Asn | Glu | Leu | Ser |
| 210 | | | | | 215 | | | | | 220 | | | | | |

| Leu | Asp | Gly | Phe | Arg | Ile | Asp | Ala | Ala | Lys | His | Ile | Lys | Phe | Ser | Phe |
| 225 | | | | | 230 | | | | | 235 | | | | | 240 |

| Leu | Arg | Asp | Trp | Val | Gln | Ala | Val | Arg | Gln | Ala | Thr | Gly | Lys | Glu | Met |
| | | | | 245 | | | | | 250 | | | | | 255 | |

| Phe | Thr | Val | Ala | Glu | Tyr | Trp | Gln | Asn | Asn | Ala | Gly | Lys | Leu | Glu | Asn |
| | | | 260 | | | | | 265 | | | | | 270 | | |

| Tyr | Leu | Asn | Lys | Thr | Ser | Phe | Asn | Gln | Ser | Val | Phe | Asp | Val | Pro | Leu |
| | | | 275 | | | | | 280 | | | | | 285 | | |

| His | Phe | Asn | Leu | Gln | Ala | Ala | Ser | Ser | Gln | Gly | Gly | Gly | Tyr | Asp | Met |
| | 290 | | | | | 295 | | | | | 300 | | | | |

| Arg | Arg | Leu | Leu | Asp | Gly | Thr | Val | Val | Ser | Arg | His | Pro | Glu | Lys | Ala |
| 305 | | | | | 310 | | | | | 315 | | | | | 320 |

| Val | Thr | Phe | Val | Glu | Asn | His | Asp | Thr | Gln | Pro | Gly | Gln | Ser | Leu | Glu |
| | | | | 325 | | | | | 330 | | | | | 335 | |

| Ser | Thr | Val | Gln | Thr | Trp | Phe | Lys | Pro | Leu | Ala | Tyr | Ala | Phe | Ile | Leu |
| | | | 340 | | | | | 345 | | | | | 350 | | |

| Thr | Arg | Glu | Ser | Gly | Tyr | Pro | Gln | Val | Phe | Tyr | Gly | Asp | Met | Tyr | Gly |
| | | | 355 | | | | | 360 | | | | | 365 | | |

| Thr | Lys | Gly | Thr | Ser | Pro | Lys | Glu | Ile | Pro | Ser | Leu | Lys | Asp | Asn | Ile |
| | 370 | | | | | 375 | | | | | 380 | | | | |

```
Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
            405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 7
<211> LENGTH: 485
<212> TYPE: PRT
<213> ORGANISM: Bacillus sp.

<400> SEQUENCE: 7

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270
```

```
Gly Ala Ile Glu Asn Tyr Leu Asn Lys Thr Ser Trp Asn His Ser Val
            275                 280                 285

Phe Asp Val Pro Leu His Tyr Asn Leu Tyr Asn Ala Ser Asn Ser Gly
        290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
                340                 345                 350

Tyr Ala Leu Val Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
                485

<210> SEQ ID NO 8
<211> LENGTH: 485
<212> TYPE: PRT
<213> ORGANISM: Bacillus halmapalus

<400> SEQUENCE: 8

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160
```

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 9
<211> LENGTH: 485
<212> TYPE: PRT
<213> ORGANISM: Bacillus sp.

<400> SEQUENCE: 9

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp

```
                35                  40                  45
Lys Gly Ala Ser Gln Asn Asp Val Gly Tyr Gly Ala Tyr Asp Leu Tyr
 50                  55                  60

Asp Leu Gly Glu Phe Asn Gln Lys Gly Thr Ile Arg Thr Lys Tyr Gly
 65                  70                  75                  80

Thr Arg Asn Gln Leu Gln Ala Ala Val Asn Ala Leu Lys Ser Asn Gly
                 85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
                115                 120                 125

Gln Glu Val Ser Gly Glu Tyr Thr Ile Glu Ala Trp Thr Lys Phe Asp
                130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
                180                 185                 190

Thr Glu Asn Gly Asn Tyr Asp Tyr Leu Met Tyr Ala Asp Ile Asp Met
                195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
                260                 265                 270

Gly Ala Ile Glu Asn Tyr Leu Asn Lys Thr Asn Trp Asn His Ser Val
                275                 280                 285

Phe Asp Val Pro Leu His Tyr Asn Leu Tyr Asn Ala Ser Lys Ser Gly
                290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Lys Ser
                370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Asn Lys Trp Met Phe Val Gly Arg Asn Lys Ala Gly
                435                 440                 445

Gln Val Trp Thr Asp Ile Thr Gly Asn Arg Ala Gly Thr Val Thr Ile
                450                 455                 460
```

```
Asn Ala Asp Gly Trp Gly Asn Phe Ser Val Asn Gly Gly Ser Val Ser
465                 470                 475                 480

Ile Trp Val Asn Lys
            485

<210> SEQ ID NO 10
<211> LENGTH: 485
<212> TYPE: PRT
<213> ORGANISM: Bacillus sp.

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
```

```
            340                 345                 350
Cys Ala Leu Thr Leu Thr Arg Asp Gln Gly Tyr Pro Ser Val Phe Tyr
            355                 360                 365
Gly Asp Tyr Tyr Gly Ile Pro Thr His Gly Val Pro Ala Met Lys Ser
            370                 375                 380
Lys Ile Asp Pro Ile Leu Glu Ala Arg Gln Lys Tyr Ala Tyr Gly Lys
385                 390                 395                 400
Gln Asn Asp Tyr Leu Asp His His Asn Met Ile Gly Trp Thr Arg Glu
                    405                 410                 415
Gly Asn Thr Ala His Pro Asn Ser Gly Leu Ala Thr Ile Met Ser Asp
                    420                 425                 430
Gly Pro Gly Gly Asn Lys Trp Met Tyr Val Gly Arg Asn Lys Ala Gly
                    435                 440                 445
Gln Val Trp Arg Asp Ile Thr Gly Asn Arg Ser Gly Thr Val Thr Ile
                    450                 455                 460
Asn Ala Asp Gly Trp Gly Asn Phe Ser Val Asn Gly Ser Val Ser
465                 470                 475                 480
Ile Trp Val Asn Asn
                485

<210> SEQ ID NO 11
<211> LENGTH: 485
<212> TYPE: PRT
<213> ORGANISM: Bacillus sp.

<400> SEQUENCE: 11

His His Asn Gly Thr Asn Gly Thr Met Met Gln Tyr Tyr Glu Trp Tyr
1               5                   10                  15
Leu Pro Asn Asp Gly Asn His Trp Asn Arg Leu Asn Ser Asp Ala Ser
                    20                  25                  30
Asn Leu Lys Ser Lys Gly Ile Thr Ala Val Trp Ile Pro Pro Ala Trp
                35                  40                  45
Lys Gly Ala Ser Gln Asn Asp Val Gly Tyr Gly Ala Tyr Asp Leu Tyr
            50                  55                  60
Asp Leu Gly Glu Phe Asn Gln Lys Gly Thr Val Arg Thr Lys Tyr Gly
65                  70                  75                  80
Thr Arg Ser Gln Leu Gln Ala Ala Val Thr Ser Leu Lys Asn Asn Gly
                        85                  90                  95
Ile Gln Val Tyr Gly Asp Val Val Met Asn His Lys Gly Gly Ala Asp
                    100                 105                 110
Ala Thr Glu Met Val Arg Ala Val Glu Val Asn Pro Asn Asn Arg Asn
                115                 120                 125
Gln Glu Val Thr Gly Glu Tyr Thr Ile Glu Ala Trp Thr Arg Phe Asp
            130                 135                 140
Phe Pro Gly Arg Gly Asn Thr His Ser Ser Phe Lys Trp Arg Trp Tyr
145                 150                 155                 160
His Phe Asp Gly Val Asp Trp Asp Gln Ser Arg Arg Leu Asn Asn Arg
                            165                 170                 175
Ile Tyr Lys Phe Arg Gly His Gly Lys Ala Trp Asp Trp Glu Val Asp
                    180                 185                 190
Thr Glu Asn Gly Asn Tyr Asp Tyr Leu Met Tyr Ala Asp Ile Asp Met
                195                 200                 205
Asp His Pro Glu Val Val Asn Glu Leu Arg Asn Trp Gly Val Trp Tyr
            210                 215                 220
```

```
Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
        260                 265                 270

Gly Ala Ile Glu Asn Tyr Leu Gln Lys Thr Asn Trp Asn His Ser Val
    275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
            325                 330                 335

Glu Glu Ala Leu Glu Ser Phe Val Glu Glu Trp Phe Lys Pro Leu Ala
        340                 345                 350

Tyr Ala Leu Thr Leu Thr Arg Glu Gln Gly Tyr Pro Ser Val Phe Tyr
    355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
        420                 425                 430

Gly Ala Gly Gly Ser Lys Trp Met Phe Val Gly Arg Asn Lys Ala Gly
    435                 440                 445

Gln Val Trp Ser Asp Ile Thr Gly Asn Arg Thr Gly Thr Val Thr Ile
450                 455                 460

Asn Ala Asp Gly Trp Ala Asn Phe Ser Val Asn Gly Gly Ser Val Ser
465                 470                 475                 480

Ile Trp Val Asn Lys
            485

<210> SEQ ID NO 12
<211> LENGTH: 480
<212> TYPE: PRT
<213> ORGANISM: Bacillus sp.

<400> SEQUENCE: 12

Asp Gly Leu Asn Gly Thr Met Met Gln Tyr Tyr Glu Trp His Leu Glu
1               5                   10                  15

Asn Asp Gly Gln His Trp Asn Arg Leu His Asp Ala Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
            85                  90                  95

Val Tyr Gly Asp Val Val Met Asn His Lys Met Gly Ala Asp Phe Thr
        100                 105                 110
```

Glu Ala Val Gln Ala Val Gln Val Asn Pro Thr Asn Arg Trp Gln Asp
            115                 120                 125

Ile Ser Gly Ala Tyr Thr Ile Asp Ala Trp Thr Gly Phe Asp Phe Ser
        130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
        435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln
465                 470                 475                 480

<210> SEQ ID NO 13
<211> LENGTH: 483
<212> TYPE: PRT
<213> ORGANISM: Bacillus licheniformis

<400> SEQUENCE: 13

Ala Asn Leu Asn Gly Thr Leu Met Gln Tyr Phe Glu Trp Tyr Met Pro

```
1               5                   10                  15
Asn Asp Gly Gln His Trp Lys Arg Leu Gln Asn Asp Ser Ala Tyr Leu
                20                  25                  30
Ala Glu His Gly Ile Thr Ala Val Trp Ile Pro Pro Ala Tyr Lys Gly
                35                  40                  45
Thr Ser Gln Ala Asp Val Gly Tyr Gly Ala Tyr Asp Leu Tyr Asp Leu
                50                  55                  60
Gly Glu Phe His Gln Lys Gly Thr Val Arg Thr Lys Tyr Gly Thr Lys
65                  70                  75                  80
Gly Glu Leu Gln Ser Ala Ile Lys Ser Leu His Ser Arg Asp Ile Asn
                85                  90                  95
Val Tyr Gly Asp Val Val Ile Asn His Lys Gly Gly Ala Asp Ala Thr
                100                 105                 110
Glu Asp Val Thr Ala Val Glu Val Asp Pro Ala Asp Arg Asn Arg Val
                115                 120                 125
Ile Ser Gly Glu Tyr Leu Ile Lys Ala Trp Thr His Phe His Phe Pro
                130                 135                 140
Gly Arg Gly Ser Thr Tyr Ser Asp Phe Lys Trp Tyr Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Tyr Trp Asp Trp Glu Val Ser Asn Glu Asn Gly Asn
                180                 185                 190
Tyr Asp Tyr Leu Met Tyr Ala Asp Ile Asp Tyr Asp His Pro Asp Val
                195                 200                 205
Val Ala Glu Ile Lys Arg Trp Gly Thr Trp Tyr Ala Asn Glu Leu Gln
                210                 215                 220
Leu Asp Gly Asn Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
                260                 265                 270
Tyr Leu Asn Lys Thr Asn Phe Asn His Ser Val Phe Asp Val Pro Leu
                275                 280                 285
His Tyr Gln Phe Tyr Ala Ala Ser Thr Gln Gly Gly Gly Tyr Asp Met
                290                 295                 300
Arg Lys Leu Leu Asn Asp Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
                340                 345                 350
Thr Arg Glu Ser Gly Tyr Pro Gln Val Phe Tyr Gly Asp Met Tyr Gly
                355                 360                 365
Thr Lys Gly Asp Ser Gln Arg Glu Ile Pro Ala Leu Lys His Lys Ile
                370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
                420                 425                 430
```

Gly Gly Ala Lys Arg Met Tyr Val Gly Arg Gln Asn Ala Gly Glu Thr
            435                 440                 445

Trp Tyr Asp Ile Thr Gly Asn Arg Ser Glu Pro Val Val Ile Asn Ser
450                 455                 460

Glu Gly Trp Gly Glu Phe His Val Asn Asp Gly Ser Val Ser Ile Tyr
465                 470                 475                 480

Val Gln Arg

<210> SEQ ID NO 14
<211> LENGTH: 481
<212> TYPE: PRT
<213> ORGANISM: Artificial Sequence
<220> FEATURE:
<223> OTHER INFORMATION: Variant

<400> SEQUENCE: 14

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Ala Ile Ser
        35                  40                  45

Gln Ala Asp Val Gly Tyr Gly Ala Tyr Asp Leu Tyr Asp Leu Gly Glu
    50                  55                  60

Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Ala Gly Ala Asp Ala Thr Glu Asp
            100                 105                 110

Val Thr Ala Val Glu Val Asp Pro Ala Asp Arg Asn Arg Val Ile Ser
        115                 120                 125

Gly Glu His Leu Ile Lys Ala Trp Thr His Phe His Phe Pro Gly Arg
    130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Lys Phe Gln
                165                 170                 175

Gly Lys Thr Trp Asp Trp Glu Val Ser Asn Glu Phe Gly Asn Tyr Asp
            180                 185                 190

Tyr Leu Met Tyr Ala Asp Phe Asp Tyr Asp His Pro Asp Val Val Ala
        195                 200                 205

Glu Ile Lys Arg Trp Gly Thr Trp Tyr Ala Asn Glu Leu Gln Leu Asp
    210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Ser Asn Asp Leu Gly Ala Leu Gly Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
    290                 295                 300

```
Leu Leu Asn Gly Thr Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

Glu Ser Gly Tyr Pro Gln Val Phe Tyr Gly Asp Met Tyr Gly Thr Lys
        355                 360                 365

Gly Asp Ser Gln Arg Glu Ile Pro Ala Leu Lys His Lys Ile Glu Pro
    370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Asp Ser Ser
                405                 410                 415

Val Ala Asn Ser Gly Leu Ala Ala Leu Ile Thr Asp Gly Pro Gly Gly
            420                 425                 430

Ala Lys Arg Met Tyr Val Gly Arg Gln Asn Ala Gly Glu Thr Trp His
        435                 440                 445

Asp Ile Thr Gly Asn Arg Ser Glu Pro Val Val Ile Asn Ser Glu Gly
    450                 455                 460

Trp Gly Glu Phe His Val Asn Gly Gly Ser Val Ser Ile Tyr Val Gln
465                 470                 475                 480

Arg

<210> SEQ ID NO 15
<211> LENGTH: 481
<212> TYPE: PRT
<213> ORGANISM: Artificial sequence
<220> FEATURE:
<223> OTHER INFORMATION: Variant

<400> SEQUENCE: 15

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Ala Ile Ser
        35                  40                  45

Gln Ala Asp Val Gly Tyr Gly Ala Tyr Asp Leu Tyr Asp Leu Gly Glu
    50                  55                  60

Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Ala Gly Ala Asp Ala Thr Glu Asp
            100                 105                 110

Val Thr Ala Val Glu Val Asp Pro Ala Asp Arg Asn Arg Val Ile Ser
        115                 120                 125

Gly Glu His Leu Ile Lys Ala Trp Thr His Phe His Phe Pro Gly Arg
    130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Leu Phe Gln
                165                 170                 175

Gly Lys Thr Trp Asp Trp Glu Val Ser Asn Glu Phe Gly Asn Tyr Asp
```

```
                    180                 185                 190
Tyr Leu Met Tyr Ala Asp Tyr Asp Tyr Pro Asp Val Val Ala
        195                 200                 205

Glu Ile Thr Arg Trp Gly Thr Trp Tyr Ala Asn Glu Leu Gln Leu Asp
        210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Pro Met Phe Thr
                245                 250                 255

Val Ala Glu Tyr Trp Ser Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
        290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

Glu Ser Gly Tyr Pro Ser Val Phe Tyr Gly Asp Met Tyr Gly Thr Lys
            355                 360                 365

Gly Asp Ser Gln Arg Glu Ile Pro Ala Leu Lys His Lys Ile Glu Pro
370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Val Ser Ser
                405                 410                 415

Val Ala Asn Ser Gly Leu Ala Ala Leu Ile Thr Asp Gly Pro Gly Gly
                420                 425                 430

Ala Lys Trp Met Tyr Val Gly Arg Gln Asn Ala Gly Glu Thr Trp His
            435                 440                 445

Asp Ile Thr Gly Asn Arg Ser Glu Pro Val Val Ile Asn Ser Glu Gly
        450                 455                 460

Trp Gly Glu Phe His Val Asn Gly Gly Ser Val Ser Ile Tyr Val Gln
465                 470                 475                 480

Arg
```